US009182406B2

(12) United States Patent
Salafsky

(10) Patent No.: US 9,182,406 B2
(45) Date of Patent: Nov. 10, 2015

(54) NONLINEAR OPTICAL DETECTION OF MOLECULES COMPRISING AN UNNATURAL AMINO ACID POSSESSING A HYPERPOLARIZABILITY

(75) Inventor: Joshua S. Salafsky, Burlingame, CA (US)

(73) Assignee: Biodesy, Inc., South San Francisco, CA (US)

( * ) Notice: Subject to any disclaimer, the term of this patent is extended or adjusted under 35 U.S.C. 154(b) by 810 days.

(21) Appl. No.: 12/535,631

(22) Filed: Aug. 4, 2009

(65) Prior Publication Data

US 2010/0068144 A1 Mar. 18, 2010

Related U.S. Application Data

(60) Provisional application No. 61/137,773, filed on Aug. 4, 2008.

(51) Int. Cl.
| | |
|---|---|
| *G01N 33/53* | (2006.01) |
| *G01N 21/68* | (2006.01) |
| *G01N 33/64* | (2006.01) |
| *G01N 33/543* | (2006.01) |
| *G01N 33/68* | (2006.01) |
| *G01N 21/64* | (2006.01) |

(52) U.S. Cl.
CPC ........ *G01N 33/6803* (2013.01); *G01N 21/6428* (2013.01); *G01N 33/54373* (2013.01); *G01N 21/6445* (2013.01); *G01N 2021/6441* (2013.01)

(58) Field of Classification Search
None
See application file for complete search history.

(56) References Cited

U.S. PATENT DOCUMENTS

| | | |
|---|---|---|
| 3,253,065 A | 5/1966 | Hansen |
| 3,847,909 A | 11/1974 | Schickfluss et al. |
| 4,619,879 A | 10/1986 | Kakuta et al. |
| 4,708,871 A | 11/1987 | Geysen |
| 4,739,044 A | 4/1988 | Stabinsky |
| 4,757,141 A | 7/1988 | Fung et al. |
| 4,775,637 A | 10/1988 | Sutherland et al. |
| 4,818,710 A | 4/1989 | Sutherland et al. |
| 4,833,092 A | 5/1989 | Geysen |
| 4,844,613 A | 7/1989 | Batchelder et al. |
| 4,978,503 A | 12/1990 | Shanks et al. |
| 4,997,928 A | 3/1991 | Hobbs, Jr. |
| 5,001,209 A | 3/1991 | Wreesmann et al. |
| 5,143,854 A | 9/1992 | Pirrung et al. |
| 5,145,790 A | 9/1992 | Mattingly et al. |
| 5,156,810 A | 10/1992 | Ribi |
| 5,215,899 A | 6/1993 | Dattagupta |
| 5,223,409 A | 6/1993 | Ladner et al. |
| 5,231,191 A | 7/1993 | Woo et al. |
| 5,236,826 A | 8/1993 | Marshall |
| 5,244,813 A | 9/1993 | Walt et al. |
| 5,250,264 A | 10/1993 | Walt et al. |
| 5,252,494 A | 10/1993 | Walt |
| 5,298,741 A | 3/1994 | Walt et al. |
| 5,320,814 A | 6/1994 | Walt et al. |
| 5,324,591 A | 6/1994 | Georger, Jr. et al. |
| 5,324,633 A | 6/1994 | Fodor et al. |
| 5,376,556 A | 12/1994 | Tarcha et al. |
| 5,389,482 A | 2/1995 | Okano et al. |
| 5,403,484 A | 4/1995 | Ladner et al. |
| 5,427,908 A | 6/1995 | Dower et al. |
| 5,432,018 A | 7/1995 | Dower et al. |
| 5,432,610 A | 7/1995 | King et al. |
| 5,485,277 A | 1/1996 | Foster |
| 5,498,530 A | 3/1996 | Schatz et al. |
| 5,498,538 A | 3/1996 | Kay et al. |
| 5,512,490 A | 4/1996 | Walt et al. |
| 5,521,289 A | 5/1996 | Hainfeld et al. |
| 5,556,762 A | 9/1996 | Pinilla et al. |
| 5,571,689 A | 11/1996 | Heuckeroth et al. |
| 5,580,717 A | 12/1996 | Dower et al. |
| 5,599,627 A | 2/1997 | Aoki et al. |
| 5,624,821 A | 4/1997 | Winter et al. |
| 5,627,024 A | 5/1997 | Maruyama et al. |
| 5,631,734 A | 5/1997 | Stern et al. |
| 5,633,724 A | 5/1997 | King et al. |
| 5,648,260 A | 7/1997 | Winter et al. |
| 5,652,060 A | 7/1997 | Uchida et al. |
| 5,663,143 A | 9/1997 | Ley et al. |
| 5,696,157 A | 12/1997 | Wang et al. |
| 5,698,426 A | 12/1997 | Huse |

(Continued)

FOREIGN PATENT DOCUMENTS

| | | |
|---|---|---|
| EP | 0740 156 A1 | 10/1996 |
| EP | 0873520 B1 | 10/2002 |

(Continued)

OTHER PUBLICATIONS

Cohen et al. Probing protein electrostatics with a synthetic fluorescent amino acid. Science. 2002. vol. 296, pp. 1700-1703.*
Zhang et al. A New Strategy for the Site-Specific Modifications of Proteins in Vivo. 2003. Biochemistry. vol. 42, pp. 6735-6746.*
Hall et al. Syntheses and Photophysical Properties of Some 5(2)-Aryl-2(5)-(4-pyridyl)oxazoles and Related Oxadiazoles and Furans. J. Heterocyclic Chem. Aug.-Sep. 1992, vol. 29, pp. 1245-1273.*

(Continued)

*Primary Examiner* — Catherine S Hibbert
*Assistant Examiner* — Channing S Mahatan
(74) *Attorney, Agent, or Firm* — Wilson Sonsini Goodrich & Rosati

(57) ABSTRACT

A system for making molecules, and proteins in particular, suitable for detection by a surface-selective nonlinear optical technique. A first use of the invention is for determining a protein's structure in real space and real time. A second use of the invention is to detect a protein or its activity (conformational change). A third use of the invention is for drug screening. A further aspect of the present invention is measuring probe tilt angle orientation in an oriented protein.

14 Claims, 8 Drawing Sheets

(56) References Cited

U.S. PATENT DOCUMENTS

| | | |
|---|---|---|
| 5,723,286 A | 3/1998 | Dower et al. |
| 5,723,323 A | 3/1998 | Kauffman et al. |
| 5,734,018 A | 3/1998 | Rutter et al. |
| 5,750,373 A | 5/1998 | Garrard et al. |
| 5,763,192 A | 6/1998 | Kauffman et al. |
| 5,766,905 A | 6/1998 | Studier et al. |
| 5,770,434 A | 6/1998 | Huse |
| 5,800,992 A | 9/1998 | Fodor et al. |
| 5,814,524 A | 9/1998 | Walt et al. |
| 5,821,060 A | 10/1998 | Arlinghaus et al. |
| 5,834,758 A | 11/1998 | Trulson et al. |
| 5,847,400 A | 12/1998 | Kain et al. |
| 5,962,248 A | 10/1999 | Tadano et al. |
| 6,023,540 A | 2/2000 | Walt et al. |
| 6,025,601 A | 2/2000 | Trulson et al. |
| 6,030,787 A | 2/2000 | Livak et al. |
| 6,040,586 A | 3/2000 | Slettnes |
| 6,055,051 A | 4/2000 | Eisenthal |
| 6,084,991 A | 7/2000 | Sampas |
| 6,095,555 A | 8/2000 | Becker et al. |
| 6,096,497 A | 8/2000 | Bauer et al. |
| 6,110,426 A | 8/2000 | Shalon et al. |
| 6,121,983 A | 9/2000 | Fork et al. |
| 6,124,102 A | 9/2000 | Fodor et al. |
| 6,134,002 A | 10/2000 | Stimson et al. |
| 6,180,415 B1 | 1/2001 | Schultz et al. |
| 6,194,222 B1 | 2/2001 | Buechler et al. |
| 6,228,326 B1 | 5/2001 | Boxer et al. |
| 6,284,197 B1 | 9/2001 | Abbott et al. |
| 6,410,245 B1 | 6/2002 | Northrup et al. |
| 6,455,303 B1 | 9/2002 | Orwar et al. |
| 6,456,423 B1 | 9/2002 | Nayfeh et al. |
| 6,576,478 B1 | 6/2003 | Wagner et al. |
| 6,682,942 B1 | 1/2004 | Wagner et al. |
| 6,699,719 B2 | 3/2004 | Yamazaki et al. |
| 6,753,200 B2 | 6/2004 | Craighead et al. |
| 6,775,003 B2 | 8/2004 | Ivarsson |
| 6,882,420 B2 | 4/2005 | Rassman et al. |
| 6,917,726 B2 | 7/2005 | Levene et al. |
| 6,953,694 B2 * | 10/2005 | Salafsky et al. ............... 436/164 |
| 7,013,054 B2 | 3/2006 | Levene et al. |
| 7,033,764 B2 | 4/2006 | Korlach et al. |
| 7,045,337 B2 | 5/2006 | Schultz et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,108,970 B2 | 9/2006 | Levinson |
| 7,126,688 B2 | 10/2006 | Rassman et al. |
| 7,181,122 B1 | 2/2007 | Levene et al. |
| 7,193,711 B2 | 3/2007 | Rassman et al. |
| 7,233,391 B2 | 6/2007 | Schermer et al. |
| 7,262,866 B2 | 8/2007 | Ivarsson |
| 7,292,742 B2 | 11/2007 | Levene et al. |
| 7,316,769 B2 | 1/2008 | Craighead et al. |
| 7,336,359 B1 | 2/2008 | Simpson et al. |
| 7,336,389 B2 | 2/2008 | Silverbrook et al. |
| 7,361,466 B2 | 4/2008 | Korlach et al. |
| 7,384,773 B1 | 6/2008 | Benson et al. |
| 7,406,222 B2 | 7/2008 | Kornilovich |
| 7,416,844 B2 | 8/2008 | Korlach et al. |
| 7,470,549 B2 | 12/2008 | Yamamoto et al. |
| 7,473,361 B2 | 1/2009 | Craighead et al. |
| 7,485,424 B2 | 2/2009 | Korlach et al. |
| 7,518,764 B2 | 4/2009 | Osborne et al. |
| 7,545,494 B2 | 6/2009 | Haiml et al. |
| 7,545,501 B2 | 6/2009 | Muraishi et al. |
| 7,563,624 B2 | 7/2009 | Ezoe et al. |
| 7,709,808 B2 | 5/2010 | Reel et al. |
| 7,833,398 B2 | 11/2010 | Craighead et al. |
| 7,943,305 B2 | 5/2011 | Korlach et al. |
| 7,943,307 B2 | 5/2011 | Korlach et al. |
| 8,039,270 B2 | 10/2011 | Dultz et al. |
| 8,062,900 B2 | 11/2011 | Modavis |
| 8,139,288 B2 | 3/2012 | Osborne et al. |
| 8,355,133 B2 | 1/2013 | Dultz et al. |
| 8,497,073 B2 | 7/2013 | Salafsky |
| 2002/0037529 A1 | 3/2002 | Fesik et al. |
| 2002/0094520 A1 | 7/2002 | Salafsky et al. |
| 2002/0094528 A1 | 7/2002 | Salafsky |
| 2002/0127563 A1 | 9/2002 | Salafsky |
| 2003/0148391 A1 | 8/2003 | Salafsky |
| 2004/0091955 A1 * | 5/2004 | Forster et al. ............... 435/68.1 |
| 2004/0146460 A1 | 7/2004 | Salafsky |
| 2005/0118731 A1 | 6/2005 | Salafsky |
| 2006/0046134 A1 | 3/2006 | Cho et al. |
| 2006/0228725 A1 | 10/2006 | Salafsky |
| 2009/0032592 A1 | 2/2009 | Christensen |
| 2010/0068144 A1 | 3/2010 | Salafsky |
| 2010/0120164 A1 | 5/2010 | Salafsky |
| 2012/0202296 A1 | 8/2012 | Eisenthal |
| 2012/0214164 A1 | 8/2012 | Densham |
| 2013/0129628 A1 | 5/2013 | Pantazis et al. |
| 2013/0288271 A1 | 10/2013 | Salafsky |
| 2014/0113312 A1 | 4/2014 | Salafsky |
| 2014/0178896 A1 | 6/2014 | Salafsky |
| 2014/0178897 A1 | 6/2014 | Salafsky |
| 2014/0186854 A1 | 7/2014 | Salafsky |
| 2014/0187431 A1 | 7/2014 | Salafsky |
| 2014/0187432 A1 | 7/2014 | Salafsky |
| 2014/0187433 A1 | 7/2014 | Salafsky |

FOREIGN PATENT DOCUMENTS

| | | |
|---|---|---|
| EP | 1798555 A1 | 6/2007 |
| JP | 11 119270 A | 4/1999 |
| WO | WO 84/03506 A1 | 9/1984 |
| WO | WO 84/03564 A1 | 9/1984 |
| WO | WO 90/05317 A1 | 5/1990 |
| WO | WO 94/29351 A2 | 12/1994 |
| WO | WO 95/34683 A1 | 12/1995 |
| WO | WO 97/09446 A1 | 3/1997 |
| WO | WO 97/15390 A1 | 5/1997 |
| WO | WO 97/35196 A1 | 9/1997 |
| WO | WO 97/46251 A1 | 12/1997 |
| WO | WO 97/47314 A1 | 12/1997 |
| WO | WO 98/14277 A1 | 4/1998 |
| WO | WO 98/15833 A1 | 4/1998 |
| WO | WO 98/20036 A1 | 5/1998 |
| WO | WO 98/20159 A1 | 5/1998 |
| WO | WO 98/20169 A1 | 5/1998 |
| WO | WO 98/51435 A1 | 11/1998 |
| WO | WO 99/51642 A1 | 10/1999 |
| WO | WO 00/00823 A1 | 1/2000 |
| WO | WO 00/39585 A1 | 7/2000 |
| WO | WO 02/44412 A1 | 6/2002 |
| WO | WO 02/46764 A1 | 6/2002 |
| WO | WO 02/054071 A1 | 7/2002 |
| WO | WO 02/61415 A1 | 8/2002 |
| WO | WO 02/095070 A2 | 11/2002 |
| WO | WO-03/0644991 A2 | 8/2003 |
| WO | WO 03/104851 A2 | 12/2003 |
| WO | WO 2012/129347 A1 | 9/2012 |
| WO | WO 2013/115867 A1 | 8/2013 |
| WO | WO 2013/162654 A1 | 10/2013 |

OTHER PUBLICATIONS

Oral Abstracts from the Society of Biomolecular Sciences 14th Annual Conference and Exhibition: St. Louis, Missouri. Apr. 6-10, 2008. J. Biomol. Screen. 2008. vol. 13, No. 7, pp. 692-721.*

Reider et al. Second-Order Nonlinear Optical Effects at Surfaces and Interfaces in Photonic Probes of Surfaces: Recent Advances. Halevi, P., editor. Elsevier Science, Amsterdam. Chapter 9, 1995, pp. 415-478.*

Zhuang et al. Mapping molecular orientation and conformation at interfaces by surface nonlinear optics. Physical Review B. May 15, 1999, vol. 59, No. 19, pp. 12632-12640.*

Abbyad, P. et al. (2007). Journal of Physical Chemistry B 111, 8269.

Achari, A. et al. (1992). Biochemistry 31, 10449.

Agrawal et al., Tetrahedron Letters, 31: 1543-1546 (1990).

Antony T. et al. (2001) A molecular beacon strategy for the thermodynamic characterization of triplex DNA: triplex formation at the promoter region of cyclin DI. Biochemistry 40, 9387-9395.

(56) References Cited

OTHER PUBLICATIONS

Aplin et al., Analyt. Biochem. 113:144-148, 1981.
Arnold S F et al. (1999) Identification of bone morphogenetic proteins and their receptors in human breast cancer cell lines: importance of BMP2. Cytokine 11, 1031-1037.
Bakhtiar, R. "Peptide nucleic acids: deoxyribonucleic acid mimics with a peptide backbone" Biochem. Educ. 26 (1998) 277-280.
Ben-Oren et al. (Sep. 1996). "Infrared Nonlinear Optical Measurements of Membrane Potential on Photoreceptor Cells," *Biophysical Journal* 71:1616-1620.
Bentin, T. et al. "Triplexes involving PNA" Triple Helix Form. Oligonucleotides (1999) 245-255.
Berkovic, G. et al. (1989). Journal of the Optical Society of America B-Optical Physics 6, 205.
Bethea (Experimental technique of dc induced SHG in liquids: measurements of the nonlinearity of $CH_2I_2$, Applied Optics, 1975, 14, 1447.
Bieri et al., "Micropatterned immobilization of a G protein-coupled receptor and direct detection of G protein activation", Nature Biotechnology, 17, 1105 (1999).
Blanchard et al., Biosens. and Bioelectron. 11 (1996) 687.
Bonnet G. et al. (1998) Kinetics of conformational fluctuations in DNA hairpin-loops. Proc Natl Acad Sci USA 95, 8602-8606.
Bouevich, A. et al. "Probing Membrane Potential with Non-linear Optics," Biophys. J. 65, 672 (1993).
Brian et al., "Allogeneic Stimulation of Cyto-toxic T-cells by Supported Planar Membranes," PNAS-Biological Sciences 81(19): 6159-6163 (1984).
Brown et al. (1999). "exploring the new world of the genome with DNA microarrays," *Nature Genet*. 21 (Suppl.) (1999), 33-37.
Brown L J et al. (2000) Molecular beacons attached to glass beads fluoresce upon hybridisation to target DNA. Chemical Comm, 621-622.
Buchardt, et al. "Peptide nucleic acids and their potential applications in biotechnology" TIBTECH 11 (1993) 384-386.
Case-Green et al., Curr. Opin. Chem. Biol. 2 (1998), 404-410.
Cha, A. et al. (1999). "Atomic Scale Movement of the Voltage-Sensing Region in a Potassium Channel Measureed via Spectroscopy," Nature 402, 809.
Chen, C.K. et al. (1981). "Detection of Molecular Monolayers by Optical Second-Harmonic Generation," Physical Review Letters 46, 1010.
Chen W et al. (2000) Molecular beacons: a real-time polymerase chain reaction assay for detecting *Salmonella*. Anal Biochem 280, 166-172.
Cheung et al., "Making and reading microarrays", Nature Genetics (Suppl.), 1999, 21:15-19.
Chrisey et al., "Covalent Attachment of Synthetic DNA to Self-Assembled Monolayer Films", Nucleic Acids Research 24, 3031, (1996).
Clarke, M.L. et al. (2005). Journal of Physical Chemistry B 109, 22027.
Clays, K. et al., (Nov. 1993). "Nonlinear Optical Properties of Proteins Measured by Hyper-Rayleigh Scattering in Solution", Science, v. 262 (5138), 1419-22.
Clayton S J et al. (2000) K-ras point mutation detection in lung cancer: comparison of two approaches to somatic mutation detection using ARMS allele-specific amplification. Clin Chem 46, 1929-1938.
Cohen, B.E. et al. (May 31, 2002). "Probing Protein Electrostatics with a Synthetic Fluorescent Amino Acid," Science 296:1700-1703.
Cohen, B.E. et al. (Jan. 25, 2005). "A Fluorescent Probe Designed for Studying Protein Conformational Change," PNAS 102(4):965-970.
Corey "Peptide nucleic acids: expanding the scope of nucleic acid recognition" TIBTECH 15 (1997) 224-229.
Craighead et al., Appl. Phys. Lett. 37:653, 1980.
Craighead et al., J. Vac. Sci. Technol. 20:316, 1982.

De Baar M P et al. (2001) Single rapid real-time monitored isothermal RNA amplification assay for quantification of Human Immunodeficiency Virus Type 1 isolates from groups M, N, and O. J Clin Microbiol 39(4):1378-1384.
Delprincipe et al. (1999). "Two Photo and UV-Laser Flash Photlysis of CA Cage Dimethoynitrophenyl-EGTA-4," Cell Calcium 2585.
De Ronde A et al. (2001) Establishment of new transmissible and drug-sensitive Human Immunodeficiency Virus Type 1 wild types due to transmission of nucleoside analogue-resistant virus. J Virol 75, 595-602.
Derrick, J.P. et al. (1992). Nature 359, 752-754.
Devor E J (2001) Use of molecular beacons to verify that the serine hydroxymethyltransferase pseudogene SHMT-psl is unique to the order primates. Genome Biol 2. 6.1-6.5.
Ditlbacher, H. et al. (2001). "Electromagnetic Interaction of Fluorophores with Designed Two-Dimensional Silver Nanoparticle Arrays," *Applied Physics B* (73) 373-377.
Dracheva S et al. (2001) N-Methyl-D-Aspartic Acid Receptor expression in Dorsolateral Prefrontal Cortex of elderly patients with schizophrenia. American Journal of Psychiatry. 158, 1400-1410.
Dubertret et al. (2001) Single-mismatch detection using gold quenched fluorescent oligonucleotides. Nat Biotechnol 19, 365-370.
Dueholm, K. L. et al. "Chemistry, properties, and applications of PNA (Peptide Nucleic Acid)" New J. Chem. 21 (1997) 19-31.
Duggan et al., Nature Genet. 21 (Suppl.) (1999), 10-14.
Durand R, et al. (2000) Use of molecular beacons to detect an antifolate resistance-associated mutation in Plasmodium falciparum. Antimicrob Agents Chemother 44, 3461-3464.
Dworczak, R. et al. Phys. Chem. Chem. Phys., 2000, 2, 5057-5064.
Eldrup et al. "Peptide nucleic acids: potential as antisense and antigene drugs" Adv. Amino Acid Mimetics Peptidomimetics 2 (1999) 221-245.
El-Hajj H H et al (2001) Detection of rifampin resistance in Mycobacterium tuberculosis in a single tube with molecular beacons. J Clin Microbiol 39, 4131-4137.
Emory et al. (1998). "Screening and Enrichment of Metal Nanoparticles with Novel Optical Properties," *J. Phys. Chem. B* 102:493-497.
Emory et al. (1998). "Direct Observation of Size-Dependent Optical Enhancement in Single Metal Nanoparticles," *J. Am. Chem. Soc.* 120: 8009-8010.
England, P.M. (2004). "Unnatural amino acid mutagenesis: A precise tool for probing protein structure and function," Biochemistry 43(37): 11623-11629.
Eun A J C et al. (2000) Molecular beacons: a new approach to plant virus detection. Phytopathology 90, 269-275.
Fang X. et al. (2000) Using molecular beacons to probe molecular interactions between lactate dehydrogenase and single-stranded DNA. Anal Chem 72, 3280-3285.
Fejer et al., IEEE Journal of Quantum Electronics, v. 28, 1992, 2631.
Felderhof, B.U. et al. (1993). Journal of the Optical Society of America B-Optical Physics 10, 1824.
Feller, M.B.et al. (1991). Physical Review A 43(12), 6778-6792.
Finn et al. J. Chem. Phys., 1974, 60, 454-458.
Fodor et al., "Light-directed Spatially-addressable Parallel Chemical Synthesis," Science, 1991, 251, 767-773.
Fortin et al. (2001). "Use of Real-Time Poylmerase Chain Reaction and Molecular Beacons for the Detection of *Escherichia coli* O157:H7," *Analytical Biochemistry* 389:281-288.
Galletto et al., *J. Phys. Chem. B* 1999, 103, 8706-8710.
Gao. et al. (1997) Messenger RNA release from ribosomes during 5'-translational blockage by consecutive low-usage arginine but not leucine codons in *Escherichia coli*. Mol Microbiol 25, 707-716.
Georger et al.,( Apr. 30 1992). "Coplanar Patterns of Self-assembled Monolayers for Selective Cell-adhesion and Outgrowth," Thin Solid Films 210 (1-2): 716-719.
Gether et al. (1995). "Fluorescent Labeling of Purified β2 Adrenergic Receptor," Journal of Biological Chemistry 270(47): 28268-28275.
Ghanouni, P. et al. (2001). PNAS 98(11) 5997-6002.
Ghanouni et al. (2001). "Functionally Different Agonists Induce Distinct Conformations in the G Protein Coupling Domain of the B2 Adrenergic Receptor", Journal of Biological Chemistry, v.276, 24433-24436.

(56) References Cited

OTHER PUBLICATIONS

Giesendorf et al.(1998) Molecular beacons: a new approach for semiautomated mutation analysis. Clin Chem 44(3): 482-486.
Giusti et al., (1993). PCR Methods and Applications, 2: 223-227.
Glauner et al. (1999). "Spectroscopic Mapping of Voltage Sensor Movement in the *Shaker* Potassium Channel," Nature 402: 813-817.
Goddard, N. et al. (Sep. 2000). "sequence Dependent Rigidity of Single Stranded DNA," Physical Review Letters 85(11): 2400-2403.
Gold, B. et al. (2001). Molecular Microbiology 42(3):851-865.
Goh, M.C. et al. (1988). "Absolute Orientation of Water-Molecules at the Neat Water-Surface," Journal of Physical Chemistry 92, 5074-5075.
Gonzalez, E. et al. (1999). PNAS 96(21):12004-12009.
Greijer, A.E. (2002) "Multiplex real-time NASBA for monitoring expression dynamics of human cytomegalovirus encoded IE1 and pp. 67 RNA" Journal of Clinical Virology 24:57-66.
Gronenborn, A.M. et al. (1991). Science 253, 657-661.
Groves, J. T. et al. "Micropatterning fluid bilayers on solid supports", Science, 1997, 275, 651-653.
Heil et al. (200). Molecular Genetics and Metabolism 71:511-519.
Heinz, T.F. (1991). "Second-Order Nonlinear Optical Effects at Surfaces and Interfaces," Elsevier: Amsterdam. Physical Review A 28(3):1883-1885.
Helmreich et al. (1996) Biochemica et Biophysica Acta 1286:285-322.
Helps C et al. (2001) Use of real-time quantitative PCR to detect Chlamydophila felis infection. J Clin Microbiol 39, 2675-2676.
Hoffmann, R., et al. "Low scale multiple array synthesis and DNA hybridization of peptide nucleic acids" Pept. Proc. Am. Pept. Symp., 15th (1999) 233-234.
Hoheisel, J. D. "Improved solid supports and spacer/linker systems for the synthesis of spatially addressable PNA libraries" Nucleosides Nucleotides 18 (1999) 1289-1291.
Huang, J. Y. et al. (1988) "Non-linear Optical Properties of Potential Sensitive Styryl Dyes", Biophysical J. 53, 665-670.
Hubbard, S.R. (1998). "Autoregulatory mechanisms in protein-tyrosine kinases," Journal of Biological Chemistry 273(20) 11987-11990.
Huse, M. et al. (2002). The conformational plasticity of protein kinases. Cell 109, 275-282.
deBaar et al. (2001). Journal of Clinical Microbiology 39(5):1895-1902.
Hyrup, B. et al. "Peptide Nucleic Acids (PNA): Synthesis, Properties and Potential Applications" Bioorg. Med. 4 (1996) 5-23.
International Search Report mailed on Feb. 10, 2006 for PCT Application No. PCT/US03/17807, 1 page.
Ishima, R. et al. (2000). Protein dynamics from NMR Nature Structural Biology vol. 7; pp. 740-743.
Jager et al. (Feb. 1996). Apply Phys Lett 68(9) 1183-1185.
Jordens J Z et al. (2000) Amplification with molecular beacon primers and reverse line blotting for the detection and typing of human papillomaviruses. J Virol Methods 89, 29-37.
Joshi, H. S. Metal-containing DNA hairpins as hybridization probes, Chem. Commun., 2001, 549-550.
Kaboev et al. (2000) PCR hot start using primers with the structure of molecular beacons (hairpin-like structure). Nucleic Acids 28(94), 2 pages.
Kamat et al. J. Phys. Chem. B, 1998, 102, 3123-3128.
Kemnitz, K. et al. (1986). "The Phase of 2nd-Harmonic Light Generated at an Interface and Its Relation to Absolute Molecular-Orientation," Chemical Physics Letters 131, 285-290.
Khatchatouriants, A. et al. Lewis, Z. Rothman, L. Loew and M. Treinin, "GFP is a Selective Non-Linear Optical Sensor of Electrophysiological Processes in C. elegans," Biophys. J. (in press, 2000) 2345-2352.
Klerks M M et al. (2001) Development of a multiplex AmpliDet RNA for the simultaneous detection of Potato leafroll virus and Potato virus Y in potato tubers. J Virol Methods 93, 115-125.
Kleinfeld et al., J. Neurosci. 8:4098-4120, 1988.

Knudsen et al. "Application of Peptide Nucleic Acid in Cancer Therapy" Anti-Cancer Drug 8 (1997) 113-118.
Kostrikis L G et al. (1998) Spectral genotyping of human alleles. Science 279, 1228-1229.
Kota, R. et al. (1999). Plant Molecular Biology Reporter 17:363-370.
Kriech, M.A. et al. (2005). "Using the intrinsic chirality of a molecule as a label-free probe to detect molecular adsorption to a surface by second harmonic generation," Applied Spectroscopy vol. 59; pp. 746-753.
Lamprecht et al., Appl. Phys. B, 1997, 64, 269-272.
Lanciotti R. S. et al. (2001) Nucleic acid sequence-based amplification assays for rapid detection of West Nile and St. Louis encephalitis viruses. J Clin Microbiol 39(12), 4506-4513.
Landry et al. Optics Express, v.5, 1999, 176-187.
Leone G. et al. (1998) Molecular beacon probes combined with amplification by NASBA enable homogeneous, real-time detection of RNA. Nucleic Acids Res 26, 2150-2155.
Levine et al. J. Chem. Phys., 1975, 63, 2666.
Levine et al. J. Chem. Phys., 1976, 65(5), 1989-1993.
Levine et al. J. Chem. Phys. 1977, 66, 1070-1074.
Levine et al. J. Chem. Phys. 1978,69(12): 5240-5245.
Lewin S R et al. (1999) Use of real-time PCR and molecular beacons to detect virus replication in human immunodeficiency virus type 1-infected individuals on prolonged effective antiretroviral therapy. J Virol 73, 6099-6103.
Lewis,A. et al. "Second Harmonic Generation of Biological Interfaces: Probing the Membrane Protein Bacteriorhodopsin and Imaging Membrane Potential Around GFP Molecules at Specific Sites in Neuronal Cells of C. elegans," Chemical Physics 245, 133-144 (1999).
Li J J. et al. (2000) Using molecular beacons as a sensitive fluorescence assay for enzymatic cleavage of single-stranded DNA. Nucleic Acids Res 28(11):e52.
Li J J et al. (2000) Molecular beacons: a novel approach to detect protein-DNA interactions. Angew Chem Int Ed 39(6): 1049-1052.
Li Q et al. (2000) Molecular beacon-based homogeneous fluorescence PCR assay for the diagnosis of infectious diseases. Analytical Sciences 16, 245-248.
Lindquist J N et al. (2000) Characterization of the interaction between alphaCP(2) and the 3'-untranslated region of collagen alpha1 (I) mRNA. Nucleic Acids Res 28, 4306-4316.
Liu et al., "Site-Directed fluorescent labeling of P-glycoprotein on cysteine residues in the nucleotide binding domains," Biochemistry 35, 11865-11873, (1996).
Liu J. et al. (2002) Real-time monitoring in vitro transcription using molecular beacons. Anal Biochem 300, 40-45.
Liu X et al. (1999) A fiber-optic evanescent wave DNA biosensor based on novel molecular beacons. Anal Chem 71, 5054-5059.
Liu, X. et al. Molecular Beacons for DNA Biosensors with Micrometer to Submicrometer Dimensions, Anal. Biochem., 283, 56-63, 2000.
Lopez et al., "Convenient Methods for Patterning the Adhesion of Mammalian Cells to Surfaces Using Self-Assembled Monolayers of Alkanethiolates on Gold," J. Am. Chem. Soc., 1993, 115, 5877-5878.
MacBeath et al. "Printing Proteins as Microarrays for High-Throughput Function Determination", Science 2000, 289, 1760-1763.
Majumdar, D.S. et al. (2007). Proceedings of the National Academy of Sciences of the United States of America 104, 12640-12645.
Manganelli R et al. (1999) Differential expression of 10 sigma factor genes in Mycobacterium tuberculosis. Mol Microbiol 31, 715-724.
Mannuzzu et al. (1996) Science 271, 213-216.
Marras et al., Multiplex detection of single-nucleotide variations using molecular beacons, S. A. E., Genetic Analysis: Biomolecular Engineering, 14 (1999), 151-156.
Marshall et al., "DNA chips—an array of possibilities," Nature Biotechnology 1998, 16(1), 27-31.
Martinson J J et al. (2000) Global distribution of the CCR2-641/CCR5-59653T HIV-1 disease-protective haplotype. Aids 14, 483-489.
Matsuo T. et al. (1998) In situ visualization of mRNA for basic fibroblast growth factor in living cells. Biochimica Biophysica Acta 1379, 178-184.

(56) References Cited

OTHER PUBLICATIONS

Matysiak, S. et al. "Improved solid supports and spacer/linker systems for the synthesis of spatially addressable PNA-libraries" Nucleosides Nucleotides 18 (1999) 1289-1291.
Mesmaeker, A. D. et al. "Backbone modifications in oligonucleotides and peptide nucleic acid systems" Curr. Opin. Struct. Biol. 5 (1995) 343-355.
McAllister et al., Am. J. Hum. Genet. 61 (Suppl.) (1997), 1387.
McConnell et al., J. Phys. Chem. B 2000, 104, 8925.
McKillip J L et al. (2000) Molecular beacon polymerase chain reaction detection of *Escherichia coli* 0157:H7 in milk. J Food Prot 63, 855-859.
Metzner K J et al. (2000) Effects of in vivo CD8(+) T cell depletion on virus replication in rhesus macaques immunized with a live, attenuated simian immunodeficiency virus vaccine. J Exp Med 191, 1921-1931.
Mrksich et al., Ann. Rev. Biophys. Biomol. Struct. 25:55-78, 1996.
Mullah B et al (1999) Efficient automated synthesis of molecular beacons. Nucleosides & Nucleotides 18, 1311-1312.
Nagar, B. et al. (2002). Crystal structures of the kinase domain of c-Abl in complex with the small molecule inhibitors PD173955 and imatinib (STI-571). Cancer Research 62, 4236-4243.
Nazarenko I A. et al. (1997) A closed tube format for amplification and detection of DNA based on energy transfer. Nucleic Acids Res 25, 2516-2521.
Nelson et al., Nucleic Acids Research, 17: 7187-7194 (1989).
Nie et al. Science, 1997, 75, 1102-1106.
Nielsen, et al. "Peptide nucleic acids-(PNA): Oligonucleotide analogues with a polyamide backbone" Antisense Research and Applications (1992) 363-372.
Nielsen, et al. "Peptide nucleic acids (PNAs): Potential Antisense and Anti-gene Agents." Anti-Cancer Drug Design 8 (1993) 53-63.
Nielsen, P. E., Egholm, M. and Buchardt, O. "Peptide Nucleic Acid (PNA). A DNA mimic with a peptide backbone" Bioconjugate Chemistry 5 (1994) 3-7.
Nielsen, P. E. "DNA analogues with nonphosphodiester backbones" Annu Rev.Biophys.Biomol.Struct. 24 (1995) 167-183.
Nielsen, P. E. et al. "Peptide nucleic acid (PNA), a new molecular tool." In Molecular Biology: Current Innovations and Future Trends, Part2. Horizon Scientific Press, (1995) 73-89.
Nielsen "Peptide nucleic acid (PNA): A lead for gene therapeutic drugs" Antisense Therapeutics 4 (1996) 76-84.
Nielsen, P. E. "Design of Sequence-Specific DNA-Binding Ligands" Chem. Eur. J. 3 (1997) 505-508.
Nielsen, P. E. and Haaima, G. "Peptide nucleic acid (PNA). A DNA mimic with a pseudopeptide backbone" Chem. Soc. Rev. (1997) 73-78.
Nielsen, P. E. "Structural and Biological Properties of Peptide Nucleic Acid (Pna)" Pure & Applied Chemistry 70 (1998) 105-110.
Nielsen "Peptide Nucleic Acids" Science and Medicine (1998) 48-55 Planning.
Nielsen, P. E. "Sequence-specific recognition of double-stranded DNA by peptide nucleic acids" Advances in DNA Sequence-Specific Agents 3 (1998) 267-278.
Nielsen "Antisense Properties of Peptide Nucleic Acid" Handbook of Experimental Pharmacology 131 (1998) 545-560.
Nielsen, P. E. "Applications of peptide nucleic acids" Curr Opin Biotechnol 10 (1999) 71-75.
Noble, et al. "Impact on Biophysical Parameters on the Biological Assessment of Peptide Nucleic Acids, Antisense Inhibitors of Gene Expression" Drug.Develop.Res. 34 (1995) 184-195.
Noble, M.E.M. et al. (2004). "Protein kinase inhibitors: Insights into drug design from structure," Science 303, 1800-1805.
Novak et al. "Assembly of Phenylacetylene-Bridged Silver and Gold Nanoparticle Arrays", J. Am. Chem. Soc., 2000, 122, 3979-3980.
Novak et al., "Nonlinear Optical Properties of Molecularly Bridged Gold Nanoparticle Arrays", J. Am. Chem. Soc. 2000, 122, 12029-12030.
Ong, S.W. et al. (1992). Chemical Physics Letters 191, 327-335.
Ortiz E et al (1998) PNA molecular beacons for rapid detection of PCR amplicons. Mol Cell Probes 12, 219-226.
Orum, H., Kessler, C. and Koch, T. "Peptide Nucleic Acid" Nucleic Acid Amplification Technologies: Application to Disease Diagnostics (1997) 29-48.
Oudar et al. J. Chem. Phys., 1977, 66, 2664-2668.
Park S et al. (2000) Rapid identification of Candida dubliniensis using a species-specific molecular beacon. J Clin Microbiol 38(8): 2829-2836.
Paszti, Z. et al. (2004). Journal of Physical Chemistry B 108, 7779.
Peleg et al., "Nonlinear optical measurement of membrane potential around single molecules at selected cellular sites," Proc. Natl. Acad. Sci. V. 96, (1999), 6700-6704.
Piatek A S et al. (1998) Molecular beacon sequence analysis for detecting drug resistance in Mycobacterium tuberculosis. Nat Biotechnol 16, 359-363.
Piatek A S et al. (2000) Genotypic analysis of Mycobacterium tuberculosis in two distinct populations using molecular beacons: implications for rapid susceptibility testing. Antimicrob Agents Chemother 44, 103-110.
Pierce K. et al. (2000) Real-time PCR using molecular beacons for accurate detection of the Y chromosome in single human blastomeres. Mol Hum Reprod 6, 1155-1164.
Poddar S. et al. (2000) Symmetric vs asymmetric PCR and molecular beacon probe in the detection of a target gene of adenovirus. Mol Cell Probes 14, 25-32.
Polizzi, M.A. et al. (2004). Journal of the American Chemical Society 126, 5001-5007.
Ramsay, "DNA chips-states-of-the-art," Nature Biotechnology 1998, 16(1), 40-44.
Rhee, J.T. et al. (Jun. 1999). Journal of Clinical Microbiology 37(6) 1764-1770.
Rinuy et al. Dec. 1999. "Second Harmonic Generation of Glucose Oxidase at the Air/Water Interface," Biophysical Journal, 77:3350-3355.
Rodriguez, E.A. et al. (2006) "In vivo incorporation of multiple unnatural amino acides through nonsense and frameshift suppression," Proceedings of the National Academy of Sciences of the United States of America 103, 8650-8655.
Saha B K. et al. (2001) Quantitation of HIV-1 by real-time PCR with a unique fluorogenic probe. J Virol Methods 93, 33-42.
Salafsky, J.S. et al. (2000). Journal of Physical Chemistry B 104, 7752-7755.
Salafsky, J.S. (2006). Journal of Chemical Physics 125, 074701.
Salafsky, J.S. et al. (2000). Chemical Physics Letters 319: 435-439.
Schena et al., Science 270 (1995), 467.
Schofield P. et al. (1997) Molecular beacons: trial of a fluorescence based solution hybridization technique for ecological studies with ruminal bacteria. Appl Environ Microbiol 63, 1143-1147.
Sebti, A. et al. (Apr. 2001). "*Candida dubliniensis* at a Cancer Center," *CID* 32:1034-1038.
Salafsky, J.S. (2007). "Second-harmonic generation for studying structural motion of biological molecules in real time and space," Phys Chem 9:5704-5711.
Gupta, K.C. et al. (1991). Nucleic Acids Research, 19: 3019-3025.
Samanta, A. et al. (2000). Journal of Physical Chemistry A 104, 8972-8975.
Sauer-Eriksson, A.E. et al. (1995). Structure 3, 265-278.
Schena et al., Science 270 (1995), 467-469.
Schofield P. et al. (1997) Molecular beacons: trial of a fluorescence based solution hybridization technique for ecological studies with ruminal bacteria. Appl Environ Microbiol 63(3) 1143-1147.
Seeliger, M.A. (2005). Protein Science 14:3135-3139.
Shih, I-M. et al. (Feb. 2001). Cancer Research 61: 818-822.
Sicheri, F. (Feb. 1997). "Crystal structure of the Src family tyrosine kinase Hck," Nature 385: 602-609.
Sicheri, F. et al. (1997). "Structures of Src-family tyrosine kinases," Current Opinion in Structural Biology 7, 777-785.
Singhvi et al., Science 264:696-698, 1994.
Smit M L et al. (2001) Semiautomated DNA mutation analysis using a robotic workstation and molecular beacons. Clin Chem 47, 739-744.

(56) References Cited

OTHER PUBLICATIONS

Sokol D L. et al. (1998) Real time detection of DNA.RNA hybridization in living cells. Proc Natl Acad Sci USA 95, 11538-11543.
Sonnichsen et al., Appl. Phys. Lett., 2000, 77(19): 2949-2951.
Spargo, B. J. (Nov. 1994). *Proc Natl Acad Sci* 91:11070-11074.
Srivastava, A. et al. "Kinetics of molecular transport across a liposome bilayer," Chem. Phys. Lett. 292 (3): 345-351 (1998).
Singer, K.D. (Oct. 1981). J Chem Phys 75(7):3572-3580.
Steemers F J et al. (2000) Screening unlabeled DNA targets with randomly ordered fiber-optic gene arrays. Nat Biotechnol 18, 91-94.
Steuerwald N et al. (1999) Analysis of gene expression in single oocytes and embryos by real-time rapid cycle fluorescence monitored RT-PCR. Mol Hum Reprod 5, 1034-1039.
Strouse R J. et al. (2000) Using molecular beacons to quantify low levels of type I endonuclease activity. Biopharm 13, 40-47.
Suh et al. Proc. SPIE 382:199, 1983.
Summerer, D. et al. (2006). "A genetically encoded fluorescent amino acid," Proceedings of the National Academy of Sciences of the United States of America 103, 9785-9789.
Szuhai K et al. (2001) Simultaneous A8344G heteroplasmy and mitochondrial DNA copy number quantification in myoclonus epilepsy and ragged-red fibers (MERRF) syndrome by a multiplex molecular beacon based real-time fluorescence PCR. Nucleic Acids Res 29(3) E13.
Szuhai K et al. (2001) A novel strategy for human papillomavirus detection and genotyping with SybrGreen and molecular beacon polymerase chain reaction. Am J Pathol 159(5):1651-1660.
Tan W. et al. (2000) Molecular beacons: a novel DNA probe for nucleic acid and protein studies. Chemistry 6, 1107-1 1111.
Tapp I et al (2000) Homogeneous scoring of single-nucleotide polymorphisms: comparison of the 5'-nuclease TaqMan assay and molecular beacon probes. Biotechniques 28, 732-738.
Thelwell N. et al. (2000) Mode of action and application of scorpion primers to mutation detection. Nucleic Acids Res 28, 3752-3761.
Thomas, G.J.J. (1999). Annual Review of Biophysics and Biomolecular Structure vol. 28; pp. 1-27.
Tung, C-H et al. (2000). Cancer Res 60:4953-4958.
Turcatti et al., "Probing the Structure and Function of the Tachykinin Neurokinin-Receptor through Biosynthetic incorporation of fluorescent amino acids at specific sites," J. Biol. Chem. 271, 19991-19998, (1996).
Bonnet, G. (May 1999). Thermodynamic basis of the enhanced specificity of structured DNA probes. Proc Natl Acad Sci USA 96, 6171-6176.
Tyagi et al., Molecular Beacons: Probes that Fluoresce upon Hybridization, Nature Biotechnology, v. 14, 1996, 303-308.
Tyagi S. et al. (1998) Multicolor molecular beacons for allele discrimination. Nat Biotechnol 16, 49-53.
Tyagi et al. Wavelength-shifting molecular beacons, Nature Biotechnology, v. 18, 2000, 1191-1196.
Uhlmann, E. "Peptide nucleic acids (PNA) and PNA-DNA chimeras: from high binding affinity towards biological function" Biol Chem 379 (1998) 1045-52.
Uhlmann, E. et al. "PNA: Synthetic polyamide nucleic acids with unusual binding properties" Angewandte Chemie-International Edition 37 (1998) 2797-2823.
Valentin, A. (2000). Virology 269:294-304.
Van Beuningen R. et al. (2001) Development of a high-throughput detection system for HIV-1 using real-time NASBA based on molecular beacons. Proceedings—SPIE the International Society for Optical Engineering. 4264, 66-71.
Van Schie R C. et al. (2000) Semiautomated clone verification by real-time PCR using molecular beacons. Biotechniques 29, 1296-1306.
Vance, F W et al., Enormous Hyper-Rayleigh Scattering from Nanocrystalline Gold Particle Suspensions, J. Phys. Chem. B 102:10091-93 (1999).
Vet J A. et al. (1999) Multiplex detection of four pathogenic retroviruses using molecular beacons. Proc Natl Acad Sci USA 96, 6394-6399.
Vogelstein B et al. (1999) Digital PCR. Proc Natl Acad Sci USA 96, 9236 9241.
Wang "DNA biosensors based on peptide nucleic acid (PNA) recognition layers. A review" Biosens Bioelectron 13 (1998) 757-62.
Watson et al. Technology for microarray analysis of gene expression, Current Opinion in Biotechnology, 9, 609-614, 1998.
Weber, G. et al. (1979). Biochemistry 18, 3075-3078.
Doring, K. et al. (2000). Protein Science 9:2246-2250.
Weisz, K. "Polyamides as artificial regulators of gene expression" Angew. Chem. Int. Ed. Eng 36 (1997) 2592-2594.
Weljie, A.M. et al. (2003). "Protein conformational changes studied by diffusion NMR spectroscopy: Application to helix-loop-helix calcium binding proteins," Protein Science vol. 12: 228-235.
Whitcombe D. et al. (1999) Detection of PCR products using self-probing amplicons and fluorescence. Nat Biotechnol 17, 804-807.
Wittung, P., Nielsen, P. and Norden, B. "Recognition of double-stranded DNA by peptide nucleic acid" Nucleosid. Nucleotid. 16 (1997) 599-602.
Xiao G et al. (2000) A DNA damage signal is required for p53 to activate gadd45. Cancer Res 60, 1711-1719.
Xie, J.M. et al. (2006). "Innovation: A chemical toolkit for proteins—an expanded genetic code," Nature Reviews Molecular Cell Biology 7, 775-782.
Xu, W.Q. et al. (1997). "Three-dimensional structure of the tyrosine kinase c-Src," Nature 385, 595-602.
Xu, W. (May 1999). Molecular Cell 3:629-638.
Yamamoto R. et al. (2000) Molecular beacon aptamer fluoresces in the presence of Tat protein of HIV-1. Genes Cells 5, 389-396.
Yates, S. et al. (2001). J Clin Microbiol 39(10): 3656-3665.
Ying L. et al. (2001) Two-state model of conformational fluctuation in a DNA hairpin-loop. Chemical Physics Letters 334, 145-150.
Zhang P. et al. (2001) Design of a molecular beacon DNA probe with two fluorophores. Angew. Chem. Int. Ed. 40, 402-405.
Zhang, B.L. et al. (1999). J Exp Med 190(5):725-732.
Zimdars, D. et al. (2001). "Static and Dynamic Solvation at the Air/Water Interface," Journal of Physical Chemistry B vol. 105; pp. 3993-4002.
Zuckerman et al., Nucleic Acids Research, 15: 5305-5321 (1987).
Lazurkin, Y.S. (1999) Molecular Biology 33(1):79-83.
Levicky et al. "Using Self-Assembly to Control the Structure of DNA Monolayers on Gold: A Neutron Reflectivity Study," Journal of the American Chemical Society 120: 9787-9792 (1998).
Oudar, J. L. (1977). The Journal of Chemical Physics 67(2): 446-457.
Sigel, G. B. (1996). Anal Chem 68:490-497.
Sproat, B. S. (1987). Nucleic Acid Research 15(12):4837-4848.
Vance, F.W. (1998). J Phys Chem 102:10091-10093.
Final Office Action mailed on Mar. 24, 2008, for U.S. Appl. No. 11/327,199, filed Jan. 5, 2006, 9 pages.
Final Office Action mailed on Feb. 16, 2012, for U.S. Appl. No. 12/571,342, filed Sep. 30, 2009, 17 pages.
Heinz, T.F. et al. (Sep. 1983). "Determination of Molecular Orientation of Monolayer Adsorbates by Optical Second-Harmonic Generation," *Physical Review A* 28:1883-1885.
Non-Final Office Action mailed on Jun. 18, 2007 for U.S. Appl. No. 11/327,199, filed Jan. 5, 2006, 7 pages.
Non-Final Office Action mailed on Mar. 30, 2009 for U.S. Appl. No. 11/327,199, filed Jan. 5, 2006, 8 pages.
Non-Final Office Action mailed on Feb. 16, 2011 for U.S. Appl. No. 12/571,342, filed Sep. 30, 2009, 14 pages.
Non-Final Office Action mailed on Oct. 2, 2012 for U.S. Appl. No. 12/571,342, filed Sep. 30, 2009, 8 pages.
Notice of Allowance mailed on May 6, 2013 for U.S. Appl. No. 12/571,342, filed Sep. 30, 2009, 9 pages.
Poddar, S. (1999). "Detection of Adenovirus Using PCR and Molecular Beacon," *J Virol Methods* 82:19-26.
Request for Continued Examination filed on Jan. 13, 2009 for U.S. Appl. No. 11/327,199, filed Jan. 5, 2006, 6 pages.
Request for Continued Examination filed on Jul. 16, 2012 for U.S. Appl. No. 12/571,342, filed Sep. 30, 2009, 10 pages.
Response to Non-Final Office Action filed on Dec. 14, 2007 for U.S. Appl. No. 11/327,199, filed Jan. 5, 2006, 8 pages.
Response to Non-Final Office Action filed on Aug. 18, 2011 for U.S. Appl. No. 12/571,342, filed Sep. 30, 2009, 6 pages.

(56) References Cited

OTHER PUBLICATIONS

Response to Non-Final Office Action filed on Apr. 1, 2013 for U.S. Appl. No. 12/571,342, filed Sep. 30, 2009, 9 pages.
Response to Restriction Requirement filed on Apr. 23, 2007 for U.S. Patent Appl. No. 11/327,199, filed Jan. 5, 2006, 5 pages.
Response to Restriction Requirement filed on Nov. 22, 2010 for U.S. Appl. No. 12/571,342, filed Sep. 30, 2009, 4 pages.
Restriction Requirement mailed on Oct. 5, 2005, for U.S. Appl. No. 10/164,915, filed Jun. 6, 2002, 4 pages.
Restriction Requirement mailed on Nov. 21, 2006, for U.S. Appl. No. 11/327,199, filed Jan. 5, 2006, 10 pages.
Restriction Requirement mailed on Jul. 13, 2010, for U.S. Appl. No. 12/571,342, filed Sep. 30, 2009, 6 pages.
Salafsky, J.S. (Oct. 6, 2003, e-published Nov. 4, 2003). "Second-Harmonic Generation as a Probe of Conformational Change in Molecules," *Chemical Physics Letters* 381:705-709.
Salafsky, J.S. et al. (2004, e-published Feb. 12, 2004). "Protein Adsorption at Interfaces Detected by Second Harmonic Generation," Additions and Corrections, *J. Phys. Chem. B* 108(10) 2000, vol. 104 B, 1 page.
Salafsky, J. (Apr. 2008). "Second-Harmonic Generation (SHG) for Identification of Allosteric & Conformation-Specific Compounds" PowerPoint Presentation presented to SBS, 30 pages.
Salafsky, J.S. et al. (Apr. 28, 2008, e-published Oct. 18, 2008). "A Second-Harmonic-Active Unnatural Amino Acid as a Structural Probe of Biomolecules," *J Phys Chem* 112:15103-15107.
Salafsky, J. (Apr. 15, 2009). "Detection Method for Conformational Change Second-Harmonic Generation Provides a Molecular-Level, Functional Readout in Real Time" *Gen Eng & Biotech News*, 2 pages.
Theodossiou, T. (2002). "Thermally Induced Irreversible Conformational Changes in Collagen Probed by Optical Second Harmonic Generation and Laser-Induced Fluorescence", *Laser Med Sci* 17:34-41.
Wang, H. et al. (1997). "Polarity of Liquid Interfacesby Second Harmonic Generation Spectroscopy," *J Phys Chem A* 101(4)713-718.
Yang, L. et al. (Date Unknown). "Surface Second Harmonic Generation (SSHG)—A New Scheme for Immunoassay," *SPIE* 2676:290-296.
U.S. Appl. No. 60/253,862, filed Nov. 29, 2000, Salafsky.
U.S. Appl. No. 60/260,249, filed Jan. 8, 2001, Salafsky.
U.S. Appl. No. 60/260,261, filed Jan. 8, 2001, Salafsky.
U.S. Appl. No. 60/260,300, filed Jan. 8, 2001, Salafsky.
U.S. Appl. No. 60/262,214, filed Jan. 17, 2001, Salafsky.
U.S. Appl. No. 60/265,775, filed Feb. 1, 2001, Salafsky.
U.S. Appl. No. 60/278,941, filed Mar. 27, 2001, Salafsky.
U.S. Appl. No. 60/306,040, filed Jul. 17, 2001, Salafsky.
U.S. Appl. No. 60/347,821, filed Oct. 23, 2001, Salafsky.
U.S. Appl. No. 60/350,322, filed Jan. 17, 2002, Salafsky.
Abel, et al. Fiber-optic evanescent wave biosensor for the detection of oligonucleotides.. Anal. Chem. 1996; 68:2905-2912.
Abrams, et al. Mutant ras epitopes as targets for cancer vaccines. Semin Oncol. Feb. 1996;23(1):118-34.
Aggarwal, et al. Contribution of the S4 segment to gating charge in the Shaker K+ channel. Neuron. Jun. 1996;16(6):1169-77.
Annis, et al. A general technique to rank protein-ligand binding affinities and determine allosteric versus direct binding site competition in compound mixtures. J Am Chem Soc. Dec. 1, 2004;126(47):15495-503.
Antikainen, et al. Conformation coupled enzyme catalysis: single-molecule and transient kinetics investigation of dihydrofolate reductase. Biochemistry. Dec. 27, 2005;44(51):16835-43.
Arnold. Metal-affinity separations: a new dimension in protein processing. Biotechnology (N Y). Feb. 1991;9(2):151-156.
Austermuhle, et al. Maltose-binding protein is open in the catalytic transition state for ATP hydrolysis during maltose transport. J Biol Chem. Jul. 2, 2004;279(27):28243-50. Epub Apr. 26, 2004.
Barlow, et al. Studies of the electronic structure of metallocene-based second-order nonlinear optical dyes. J. Am. Chem. Soc. 1999; 121:3715-3723.
Bar-Sagi. A Ras by any other name. Mol Cell Biol. Mar. 2001;21(5):1441-3.
Bertoncini, et al. Release of long-range tertiary interactions potentiates aggregation of natively unstructured alpha-synuclein. Proc Natl Acad Sci U S A. Feb. 1, 2005;102(5):1430-5. Epub Jan. 25, 2005.
Bier, et al. Real-time measurement of nucleic-acid hybridization using evanescent-wave sensors: steps towards the genosensor. Sens. Actuators B Chem. 1997; 38:78-82.
Boyd, et al. Local-field enhancement on rough surfaces with the use of optical 2nd-harmonic generation. Phys. Rev. B 1984; 30:519-526.
Brooks, et al. Optimizing levodopa therapy for Parkinson's disease with levodopa/carbidopa/entacapone: implications from a clinical and patient perspective. Neuropsychiatr Dis Treat. Feb. 2008;4(1):39-47.
Campagnola, et al. High-resolution nonlinear optical imaging of live cells by second harmonic generation. Biophys J. Dec. 1999;77(6):3341-9.
Campagnola, et al. Second-harmonic imaging microscopy for visualizing biomolecular arrays in cells, tissues and organisms. Nat Biotechnol. Nov. 2003;21(11):1356-60.
Campagnola, et al. Three-dimensional high-resolution second-harmonic generation imaging of endogenous structural proteins in biological tissues. Biophysical Journal. 2002; 81:493-508.
Cha, et al. Characterizing voltage-dependent conformational changes in the Shaker K+ channel with fluorescence. Neuron. Nov. 1997;19(5):1127-40.
Chang, et al. Human genome contains four genes homologous to transforming genes of Harvey and Kirsten murine sarcoma viruses. Proc Natl Acad Sci U S A. Aug. 1982;79(16):4848-52.
Cheng, et al. Experimental investigations of organic molecular nonlinear optical polarizabilities. 1. Methods and results on benzene and stilbene derivatives. J. Phys. Chem. 1991; 95:10631-10643.
Cheng, et al. Experimental investigations of organic molecular nonlinear optical polarizabilities. 2. A study of conjugation dependencies. J. Phys. Chem. 1991; 95:10643-10652.
Christopoulos. Allosteric binding sites on cell-surface receptors: novel targets for drug discovery. Nat Rev Drug Discov. Mar. 2002;1(3):198-210.
Chung, et al. Two-Dimensional Standing Wave Total Internal Reflection Fluorescence Microscopy: Superresolution Imaging of Single Molecular and Biological Specimens. Biophys J. Sep. 1, 2007; 93(5): 1747-1757.
Clackson, et al. Making antibody fragments using phage display libraries. Nature. Aug. 15, 1991;352(6336):624-8.
Clark, et al. Second harmonic generation properties of fluorescent polymer-encapsulated gold nanoparticles. J. Am. Chem. Soc. 2000; 122:10234-10235.
Conboy, et al. Studies of Alkane/water interfaces by total internal reflection second harmonic generation. J. Phys. Chem. 1994; 98:9688-9698.
Conway, et al. Fibrils formed in vitro from alpha-synuclein and two mutant forms linked to Parkinson's disease are typical amyloid. Biochemistry. Mar. 14, 2000;39(10):2552-63.
Cwirla, et al. Peptides on phage: a vast library of peptides for identifying ligands. Proc Natl Acad Sci U S A. Aug. 1990;87(16):6378-82.
Ditcham, et al. An immunosensor with potential for the detection of viral antigens in body fluids, based on surface second harmonic generation. Biosens Bioelectron. May 2001;16(3):221-4.
Duncan, et al. The binding site for C1q on IgG. Nature. Apr. 21, 1998;332(6166):738-40.
Eckstein. Oligonucleotides and analogues. Oxford University Press. 1991.
Efimov, et al. Bacteriophage T4 as a surface display vector. Virus Genes. 1995;10(2):173-7.
Eisenthal. Photochemistry and photophysics of liquid interfaces by second harmonic spectroscopy. J. Phys. Chem. 1996; 100:12997-13006.
Ekins, et al. Microarrays: their origins and applications. Trends Biotechnol. Jun. 1999;17(6):217-8.
Elender, et al. Functionalisation of Si/SiO2 and glass surfaces with ultrathin dextran films and deposition of lipid bilayers. Biosens Bioelectron. 1996;1 1(6-7):565-77.

(56) References Cited

OTHER PUBLICATIONS

European search report Jan. 24, 2008 for EP Application No. 03736879.2, 4 pages.
European search report May 18, 2005 for EP Application No. 01995403.1, 6 pages.
European search report Dec. 3, 2004 for EP Application No. 01957166.0, 3 pages.
Falkiewicz. Peptide nucleic acids and their structural modifications. Acta Biochim Pol. 1999;46(3):509-29.
Ferguson, et al. A fiber-optic DNA biosensor microarray for the analysis of gene expression. Nat Biotechnol. Dec. 1996;14(13):1681-4.
Fernandez, et al. NMR of alpha-synuclein-polyamine complexes elucidates the mechanism and kinetics of induced aggregation. EMBO J. May 19, 2004;23(10):2039-46. Epub Apr. 22, 2004.
Fittinghoff. Collinear type II second-harmonic-generation frequency-resolved optical gating for use with high-numerical-aperature objectives, 1998, Opt Lett, 23(13), 1046-1048.
Fodor. Massively parallel genomics. Science. 1997; 277:393-395.
Frey, et al. Two-dimensional protein crystallization via metal-ion coordination by naturally occurring surface histidines. Proc Natl Acad Sci U S A. May 14, 1996;93(10):4937-41.
Friday, et al. K-ras as a target for cancer therapy. Biochim Biophys Acta. Nov. 25, 2005;1756(2):127-44. Epub Aug. 18, 2005.
Fulton, et al. Advanced multiplexed analysis with the FlowMetrix system. Clin Chem. Sep. 1997;43(9):1749-56.
Garcia-Pomar, et al. Experimental two-dimensional field mapping of total internal reflection lateral beam shift in a self-collimated photonic crystal. Appl. Phys. Lett. 94, 061121 (2009) http://dx.doi.org/10.1063/1.3085768.
Gerry, et al. Universal DNA microarray method for multiplex detection of low abundance point mutations. J Mol Biol. Sep. 17, 1999;292(2):251-62.
Geysen, et al. Small peptides induce antibodies with a sequence and structural requirement for binding antigen comparable to antibodies raised against the native protein. Proc Natl Acad Sci U S A. Jan. 1985;82(1):178-82.
Geysen, et al. Strategies for epitope analysis using peptide synthesis. J Immunol Methods. Sep. 24, 1987;102(2):259-74.
Geysen, et al. The delineation of peptides able to mimic assembled epitopes. Ciba Found Symp. 1986;119:130-49.
Geysen, et al. Use of peptide synthesis to probe viral antigens for epitopes to a resolution of a single amino acid. Proc Natl Acad Sci U S A. Jul. 1984;81(13):3998-4002.
Gliko, et al. Fast two-dimensional standing-wave total-internal-reflection fluorescence microscopy using acousto-optic deflectors. Optics Letters. 2009; 34(6):836-838.
Goodey, et al. Allosteric regulation and catalysis emerge via a common route. Nat Chem Biol. Aug. 2008;4(8):474-82. doi: 10.1038/nchembio.98.
Groves, et al. Electrical manipulation of glycan-phosphatidyl inositol-tethered proteins in planar supported bilayers. Biophys J. Nov. 1996;71(5):2716-23.
Groves, et al. Micropattern formation in supported lipid membranes. Acc Chem Res. Mar. 2002;35(3):149-57.
Gunner, et al. Electrostatic Potentials in Rhodopseudomonas Viridis Reaction Centers: Implications for the Driving Force and Directionality of Electron Transfer. J. Phys. Chem. 1996; 100:4277-4291.
Hall, et al. The structural basis for the transition from Ras-GTP to Ras-GDP. Proc Natl Acad Sci U S A. Sep. 17, 2002;99(19):12138-42. Epub Sep. 4, 2002.
Harrick. Internal reflection spectroscopy. Harrick Scientific Corporation. 2nd printing 1979.
Harrison. Variation on an Src-like Theme. Cell. 2003; 112(6):737-740.
Heath, et al. Covalent attachment of immunoglobulins to liposomes via glycosphingolipids. Biochim Biophys Acta. Jan. 8, 1981;640(1):66-81.

Heinz, et al. Spectroscopy of Molecular Monolayers by Resonant Second-Harmonic Generation. Phys. Rev. Lett. 1982; 48, 478. DOI: http://dx.doi.org/10.1103/PhysRevLett.48.478.
Hicks. Studies of Chemical Processes in Liquids Using Short Laser Pulses: 1. The Dynamics of Photoisomerization of Polar Molecules in Solution 2. Studies of Liquid Surfaces by Second Harmonic Generation Ph.D. dissertation, Columbia University. 1986.
Ho, et al. Optical sensors based on hybrid aptamer/conjugated polymer complexes. J Am Chem Soc. Feb. 11, 2004;126(5):1384-7.
Ho, et al. Optical sensors based on hybrid DNA/conjugated polymer complexes. Chemistry. Mar. 4, 2005;11(6):1718-24.
Hodgson, et al. The synthesis of peptides and proteins containing non-natural amino acids. Chem Soc Rev. Sep. 10, 2004;33(7):422-30. Epub Aug. 13, 2004.
Hubbard, et al. Nonlinear optical studies of a fluorinated poled polyimide guest-host system. Applied Physics Letters. 1994; 65(3):265-267.
International search report dated Jan. 22, 2002 for PCT/US2001/022411, 2 pages.
International search report dated Feb. 10, 2006 for PCT/US2003/017807, 1 page.
International search report dated Mar. 23, 2006 for PCT/US2002/022681, 2 pages.
International search report dated Apr. 20, 2012 for PCT/US2012/030010, 4 pages.
International search report dated May 1, 2002 for PCT/US2001/046932, 1 page.
International search report dated Oct. 20, 2001 for PCT/US2001/022412, 3 pages.
International search report dated Dec. 27, 2001 for PCT/US2001/022441, 2 pages.
Jiang, et al. Display of a PorA peptide from Neisseria meningitidis on the bacteriophage T4 capsid surface. Infect Immun. Nov. 1997;65(11):4770-7.
Joshi, et al. A three-component Mannich-type reaction for selective tyrosine bioconjugation. J Am Chem Soc. Dec. 15, 2004;126(49):15942-3.
Kajikawa, et al. Second harmonic generation in disperse-red-labeled poly(methyl methacrylate) Langmuir Blodgett film. Appl. Phys. Letters, May 3, 1993; 62(18):2161-2163.
Kang, et al. Linkage of recognition and replication functions by assembling combinatorial antibody Fab libraries along phage surfaces. Proc Natl Acad Sci U S A. May 15, 1991;88(10):4363-6.
Kang, et al. Specific adsorption of histidine-tagged proteins on silica surfaces modified with Ni2+/NTA-derivatized poly(ethylene glycol). Langmuir. May 22, 2007;23(11):6281-8. Epub Apr. 20, 2007.
Karpinar, et al. Pre-fibrillar alpha-synuclein variants with impaired beta-structure increase neurotoxicity in Parkinson's disease models. EMBO J. Oct. 21, 2009;28(20):3256-68. doi: 10.1038/emboj.2009.257. Epub Sep. 10, 2009.
Keseru, et al. Hit discovery and hit-to-lead approaches. Drug Discov Today. Aug. 2006;11(15-16):741-8.
Kleinjung, et al. Fibre-optic genosensor for specific determination of femtomolar DNA oligomers. Analytica Chimica Acta. 1997; 350:51-58.
Klockgether. Parkinson's disease: clinical aspects. Cell Tissue Res. Oct. 2004;318(1):115-20. Epub Sep. 8, 2004.
Knighton, et al. Crystal structure of the catalytic subunit of cyclic adenosine monophosphate-dependent protein kinase. Science. Jul. 26, 1991;253(5018):407-14.
Kozarac, et al. Interaction of Proteins with Lipid Monolayers at the Air-Solution Interface Studied by Reflection Spectroscopy. Eur. Biophys. J. 1987; 15:193-196.
Kufareva, et al. Type-II kinase inhibitor docking, screening, and profiling using modified structures of active kinase states. J Med Chem. Dec. 25, 2008;51(24):7921-32. doi: 10.1021/jm8010299.
Kuhner, et al. Lipid mono- and bilayer supported on polymer films: composite polymer-lipid films on solid substrates. Biophys J. Jul. 1994;67(1):217-26.
Lang, et al. Parkinson's disease. Second of two parts. N Engl J Med. Oct. 15, 1998;339(16):1130-43.
.M.1 c.S Larsson, et al. Transmembrane movement of the shaker K+ channel S4. Neuron. Feb. 1996;16(2):387-97.

(56) References Cited

OTHER PUBLICATIONS

Le Floch, et al. Label-free electrochemical detection of protein based on a ferrocene-bearing cationic polythiophene and aptamer. Analytical Chemistry 78, 4727-4731 (2006).
Levene, et al. Zero-Mode Waveguides for Single-Molecule Analysis at High Concentrations. Science. 2003; 299 (5607): 682-686.
Levine, et al. Absolute signs of hyperpolarizabilities in the liquid state. J. Chem. Phys. 1974; 60(10)3856-3858.
Levine. Conjugated electron contributions to the second order hyperpolarizability of substituted benzene molecules J. Chem. Phys. 1975; 63:115-117.
Li, et al. Filamentous bacteriophage display of a bifunctional protein A::scFv fusion. Mol Biotechnol. Jun. 1998;9(3):187-93.
Liu, et al. Rational design of inhibitors that bind to inactive kinase conformations. Nat Chem Biol. Jul. 2006;2(7):358-64.
Lorber, et al. Flexible ligand docking using conformational ensembles. Protein Sci. Apr. 1998;7(4):938-50.
Lowman, et al. Selecting high-affinity binding proteins by monovalent phage display. Biochemistry. Nov. 12, 1991;30(45):10832-8.
Lu, et al. Mutation-selective tumor remission with Ras-targeted, whole yeast-based immunotherapy. Cancer Res. Aug. 1, 2004;64(15):5084-8.
Magnuson, et al. The Raf-1 serine/threonine protein kinase.Semin Cancer Biol. Aug. 1994;5(4):247-53.
Mallik, et al. Towards materials for the specific recognition and separation of proteins. New J. Chem. 1994; 18:299-304.
Marks, et al. By-passing immunization. Human antibodies from V-gene libraries displayed on phage. J Mol Biol. Dec. 5, 1991;222(3):581-97.
Marshall, et al. DNA chips: an array of possibilities. Nat Biotechnol. Jan. 1998;16(1):27-31.
Martin, et al. Immunospecific targeting of liposomes to cells: a novel and efficient method for covalent attachment of Fab' fragments via disulfide bonds. Biochemistry. Jul. 7, 1981;20(14):4229-38.
Martin, et al. Irreversible coupling of immunoglobulin fragments to preformed vesicles. An improved method for liposome targeting. J Biol Chem. Jan. 10, 1982;257(1):286-8.
McClendon, et al. Charge neutralization and collapse of the C-terminal tail of alpha-synuclein at low pH. Protein Sci. Jul. 2009;18(7):1531-40. doi: 10.1002/pro.149.
McHugh, et al. Construction, purification, and functional incorporation on tumor cells of glycolipid-anchored human B7-1 (CD80). Proc Natl Acad Sci U S A. Aug. 15, 1995;92(17):8059-63.
Michael, et al. Randomly ordered addressable high-density optical sensor arrays. Anal Chem. Apr. 1, 1998;70(7):1242-8.
Millard, et al. Second harmonic imaging microscopy. Methods Enzymol. 2003;361:47-69.
Milosevic, et al. Extreme-ultraviolet harmonic generation near 13 nm with a two-color elliptically polarized laser field, 2000, Opt Lett, 25(20), 1532-1534.
Moreaux, et al. Membrane imaging by second harmonic generation microscopy. Journal of Optical Society of America B: Optical Physics. 2000; 17(10):1685-1694.
Nagar, et al. Structural basis for the autoinhibition of c-Abl tyrosine kinase. Cell. Mar. 21, 2003;112(6):859-71.
Needels, et al. Generation and screening of an oligonucleotide-encoded synthetic peptide library. Proc Natl Acad Sci U S A. Nov. 15, 1993;90(22):10700-4.
Neumann, et al. Functional immobilization of a ligand-activated G-protein-coupled receptor. Chembiochem. Oct. 4, 2002;3(10):993-8.
Noble, et al. Protein kinase inhibitors: insights into drug design from structure. Science. Mar. 19, 2004;303(5665):1800-5.
Norris, et al. Reversible inhibition of alpha-synuclein fibrillization by dopaminochrome-mediated conformational alterations. J Biol Chem. Jun. 3, 2005;280(22):21212-9. Epub Apr. 6, 2005.
Nye, et al. Kinetic control of histidine-tagged protein surface density on supported lipid bilayers. Langmuir. Apr. 15, 2008;24(8):4145-9. doi: 10.1021/la703788h. Epub Feb. 28, 2008.

Office action dated Feb. 7, 2002 for U.S. Appl. No. 09/731,366, 15 pages.
Office action dated Feb. 23, 2004 for U.S. Appl. No. 09/731,366, 16 pages.
Office action dated Apr. 21, 2004 for U.S. Appl. No. 09/907,038, 16 pages.
Office action dated May 8, 2002 for U.S. Appl. No. 09/907,035, 25 pages.
Office action dated Aug. 25, 2003 for U.S. Appl. No. 09/907,035, 22 pages.
Office action dated Sep. 10, 2004 for U.S. Appl. No. 09/731,366, 15 pages.
Office action dated Sep. 20, 2005 for U.S. Appl. No. 10/467,098, 10 pages.
Office action dated Oct. 23, 2003 for U.S. Appl. No. 09/731,366, 16 pages.
Office action dated Oct. 28, 2002 for U.S. Appl. No. 09/731,366, 15 pages.
Office action dated Nov. 3, 2006 for U.S. Appl. No. 10/970,754, 12 pages.
Office action dated Nov. 20, 2002 for U.S. Appl. No. 09/907,035, 25 pages.
Pantano, et al. Ordered nanowells arrays. Chem. Mater. 1996; 8:2832-2835.
Pargellis, et al. Inhibition of p38 MAP kinase by utilizing a novel allosteric binding site. Nat Struct Biol. Apr. 2002;9(4):268-72.
Perozo, et al. rearrangements underlying K+-channel activation gating. Science. Jul. 2, 1999;285(5424):73-8.
Piunno, et al. Fiber-optic DNA sensor for fluorometric nucleic acid determination. Anal Chem. Aug. 1, 1995;67(15):2635-43.
Potyrailo, et al. Adapting selected nucleic acid ligands (aptamers) to biosensors. Anal Chem. Aug. 15, 1998;70(16):3419-25.
Rajagopalan, et al. Interaction of dihydrofolate reductase with methotrexate: ensemble and single-molecule kinetics. Proc Natl Acad Sci U S A. Oct. 15, 2002;99(21):13481-6. Epub Oct. 1, 2002.
Ren, et al. Cloning of linear DNAs in vivo by overexpressed T4 DNA ligase: construction of a T4 phage hoc gene display vector. Gene. Aug. 22, 1997;195(2):303-11.
Ren, et al. Phage display of intact domains at high copy number: a system based on SOC, the small outer capsid protein of bacteriophage T4. Protein Sci. Sep. 1996;5(9):1833-43.
Ren, et al. Phage T4 SOC and HOC display of biologically active, full-length proteins on the viral capsid. Gene. Jul. 30, 1998;215(2):439-44.
Sackmann. Supported membranes: scientific and practical applications. Science. Jan. 5, 1996;271(5245):43-8.
Salafsky, et al. Architecture and function of membrane proteins in planar supported bilayers: A study with photosynthetic reaction centers' Biochemistry. 1996; 35(47):14773-14781.
Salafsky, et al. SHG labels for detection of molecules by second harmonic generation. Chemical Physics Letters. 2001; 342:485-491.
Sandberg, et al. New chemical descriptors relevant for the design of biologically active peptides. A multivariate characterization of 87 amino acids. J Med Chem. Jul. 2, 1998;41(14):2481-91.
Schindler, et al. Structural mechanism for STI-571 inhibition of abelson tyrosine kinase. Science. Sep. 15, 2000;289(5486):1938-42.
Schneider, et al. Synthesis and characterization of the first fluorescent nonpeptide NPY Y1 receptor antagonist. Chembiochem. Nov. 5, 2007;8(16):1981-8.
Schoofs, et al. Epitopes of an influenza viral peptide recognized by antibody at single amino acid resolution. J Immunol. Jan. 15, 1988;140(2):611-6.
Schwede, et al. Swiss-Model: An automated protein homology-modeling server. Nucleic Acids Res. Jul. 1, 2003;31(13):3381-5.
Scott, et al. Searching for peptide ligands with an epitope library. Science. Jul. 27, 1990;249(4967):386-90.
Seeliger, et al. c-Src binds to the cancer drug imatinib with an inactive Abl/c-Kit conformation and a distributed thermodynamic penalty. Structure. Mar. 2007;15(3):299-311.
Seeliger, et al. Equally potent inhibition of c-Src and Abl by compounds that recognize inactive kinase conformations. Cancer Res. Mar. 15, 2009;69(6):2384-92. doi: 10.1158/0008-5472.CAN-08-3953. Epub Mar. 10, 2009.

(56) References Cited

OTHER PUBLICATIONS

Shan, et al. A conserved protonation-dependent switch controls drug binding in the Abl kinase. Proc Natl Acad Sci U S A. Jan. 6, 2009;106(1):139-44. doi: 10.1073/pnas.0811223106. Epub Dec. 24, 2008.
Shen. Optical Second Harmonic Generation at Interfaces. Annual Review of Physical Chemistry. 1989; 40(1):327-350.
Shen. Surface properties probed by second-harmonic and sum-frequency generation. Nature. 1989; 337: 20 519-525.
Shen. The Principles of Nonlinear Optics, John Wiley & Sons, New York. 1984, 4 pages. Cover page, bibilographic page, and content pages only.
Shnek, et al. Specific Protein Attachment to Artificial Membranes via Coordination to Lipid-Bound Copper (II). Langmuir. 1994; 10:2382-2388.
Simard, et al. A new screening assay for allosteric inhibitors of cSrc. Nat Chem Biol. Jun. 2009;5(6):394-6. doi: 10.1038/nchembio.162. Epub Apr. 26, 2009.
Simard, et al. Development of a fluorescent-tagged kinase assay system for the detection and characterization of allosteric kinase inhibitors. J Am Chem Soc. Sep. 23, 2009;131(37):13286-96. doi: 10.1021/ja902010p.
Sittampalam, et al. High-throughput screening: advances in assay technologies. Curr Opin Chem Biol. Oct. 1997;1(3):384-91.
Smith, et al. Libraries of peptides and proteins displayed on filamentous phage. Methods Enzymol. 1993;217:228-57.
Smith. Surface presentation of protein epitopes using bacteriophage expression systems. Curr Opin Biotechnol. Oct. 1991;2(5):668-73.
Suslick, et al. Push-pull porphyrins as nonlinear optical materials. J. Am. Chem. Soc. 1992; 114:6928-6930.
Szemes, et al. Development of a multiplex AmpliDet RNA assay for simultaneous detection and typing of potato virus Y isolates. J Virol Methods. Feb. 2002;100(1-2):83-96.
Takagi, et al. Global conformational rearrangements in integrin extracellular domains in outside-in and inside-out signaling. Cell. Sep. 6, 2002;110(5):599-11.
Uddin, et al. A fiber optic biosensor for fluorimetric detection of triple-helical DNA. Nucleic Acids Res. Oct. 15, 1997;25(20):4139-46.
Van Elshocht, et al. Chiral 1,1E-binaphthyl-based helical polymers as nonlinear optical materials. Chemical Physics Letters. 1999; 309:315-320.
Verdine, et al. The challenge of drugging undruggable targets in cancer: lessons learned from targeting BCL-2 family members. Clin Cancer Res. Dec. 15, 2007;13(24):7264-70.
Vogtherr, et al. NMR characterization of kinase p38 dynamics in free and ligand-bound forms. Angew Chem Int Ed Engl. Jan. 30, 2006;45(6):993-7.
Walt. Techview: molecular biology. Bead-based fiber-optic arrays. Science. Jan. 21, 2000;287(5452):451-2.
Wang, et al. In situ, nonlinear optical probe of Surfactant Adsorption on the Surface of Microparticles in Colloids. Langmuir 2000, 16, 2475-2481.
Wennerberg, et al. The Ras superfamily at a glance. J Cell Sci. Mar. 1, 2005;118(Pt 5):843-6.
Wettstein, et al. Expression of a class II major histocompatibility complex (MHC) heterodimer in a lipid-linked form with enhanced peptide/soluble MHC complex formation at low pH. J Exp Med. Jul. 1, 1991;174(1):219-28.
Xie, et al. Adding amino acids to the genetic repertoire. Curr Opin Chem Biol. Dec. 2005;9(6):548-54. Epub Nov. 2, 2005.
Yang, et al. Spectral broadening of ultrashort pulses in a nonlinear medium. Opt Lett. Nov. 1, 1984;9(11):510-2.
Yellen. The moving parts of voltage-gated ion channels. Q Rev Biophys. Aug. 1998;31(3):239-95.
You, et al. Affinity capturing for targeting proteins into micro and nanostructures. Anal Bioanal Chem. Mar. 2009;393(6-7):1563-70. doi: 10.1007/s00216-008-2595-6. Epub Jan. 20, 2009.
Zhang, et al. A chemilluminescence fiber-optic biosensor for detection of DNA hybridization. Anal. Lett. 1999; 32:2725-2736.
Zhang, et al. Targeting cancer with small molecule kinase inhibitors. Nat Rev Cancer. Jan. 2009;9(1):28-39. doi: 10.1038/nrc2559.
Zhu, et al. Inhibition of vascular endothelial growth factor-induced receptor activation with anti-kinase insert domain-containing receptor single-chain antibodies from a phage display library. Cancer Res. Aug. 1, 1998;58(15):3209-14.

* cited by examiner

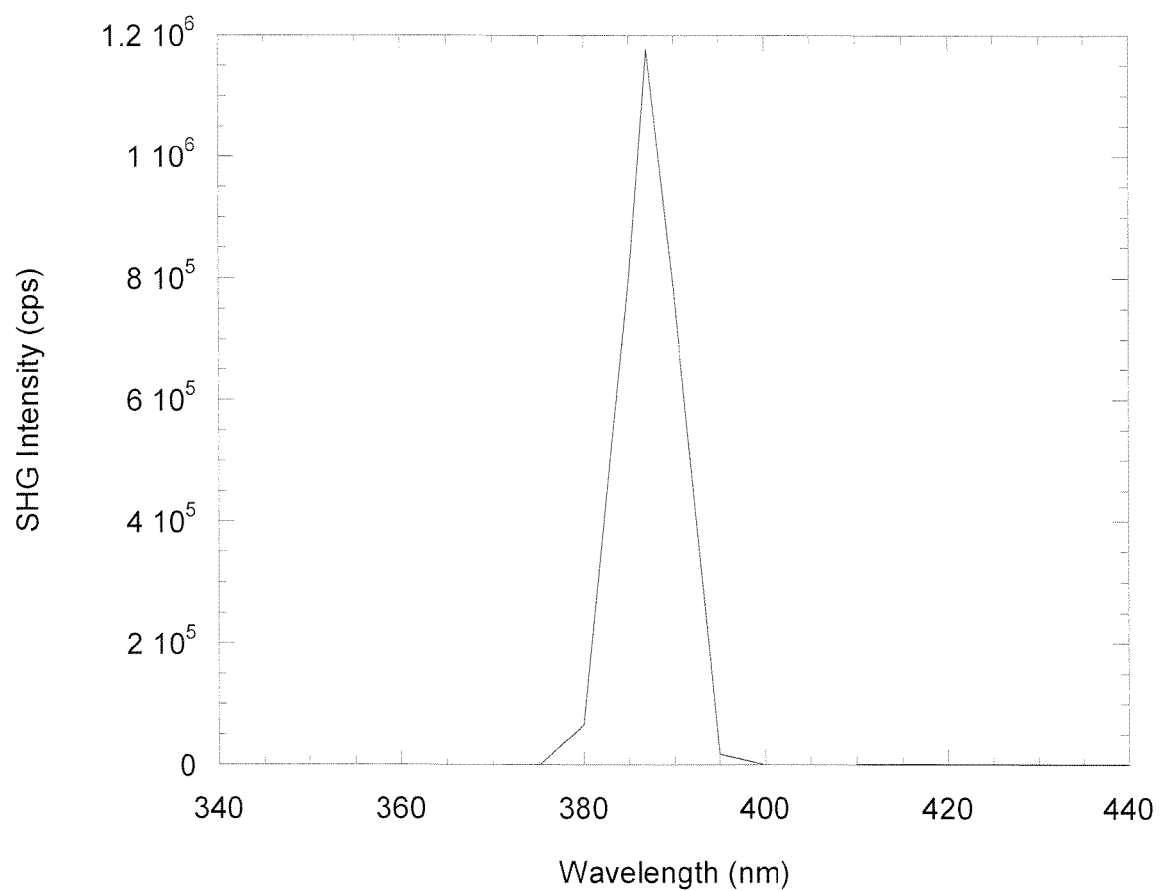

NONLINEAR OPTICAL DETECTION OF MOLECULES COMPRISING AN UNNATURAL AMINO ACID POSSESSING A HYPERPOLARIZABILITY

CROSS-REFERENCES

This application is based upon and claims the benefit under 35 U.S.C. §119(e) of U.S. Provisional Patent Application Ser. No. 61/137,773, filed Aug. 4, 2008. This application incorporates by reference in their entireties for all purposes U.S. Provisional Patent Application Ser. No. 61/137,773 and the various references cited and identified below.

INTRODUCTION

Surface-selective techniques such as second-harmonic generation (SHG) have recently been applied to the study of proteins at interfaces and protein conformational change by the use of second-harmonic-active labels[1-3], which are attached to the surface of the protein. Methods for detecting proteins by SHG or sum-frequency generation (SFG) are disclosed wherein the protein is detected by incorporating an SH-active (or SF-active) unnatural amino acid probe into it.

The aim of structure-based drug screening and basic studies of the mechanism of biological molecules requires a tool that can measure structure, and structural change, of biological molecules as they bind to ligands, drugs, etc. Present techniques for determining structural change are mainly confined to NMR (Nuclear Magnetic Resonance) and X-ray crystallography. Neither of these techniques is suitable for measuring structural change in real-time. Moreover, they are time- and labor-intensive and unsuitable for widescale use in drug screening. Furthermore, there are many proteins that are difficult to crystallize (e.g., membrane proteins) and thus whose structures have not been determined.

It is often not convenient to label a protein using standard in vitro methods, as it may require single-site mutagenesis to produce an attachment site for the chemical label, or the labeling itself may introduce a perturbative modification to the structure of the protein. Also, it is often not possible to engineer a single, chemically reactive and orthogonal attachment site for a label into a protein; for example, there may be native and reactive cysteine groups in the case of sulfhydryl-bearing labels. Furthermore, for the purpose of measuring conformational change using a surface-selective nonlinear detection technique such as second-harmonic generation (SHG) or sum-frequency generation (SFG), it is desirable to have the probe (the label) rigidly fixed within the protein frame of reference. Then, movement of the label relative to the protein will be minimized, if not completely eliminated, the signal contrast (i.e., SH signal) between conformations will be maximized, and precise spatial measurements of the probe tilt angle relative to a surface can be used to determine a protein's structure.

SUMMARY

The present invention includes a system for making molecules, and proteins in particular, suitable for detection by a surface-selective nonlinear optical technique. A first use of the invention is for determining a protein's structure in real space and real time. A second use of the invention is to detect a protein or its activity (conformational change). A third use of the invention is for drug screening A further aspect of the present invention is measuring probe tilt angle orientation in an oriented protein.

DETAILED DESCRIPTION

Figure 1A:
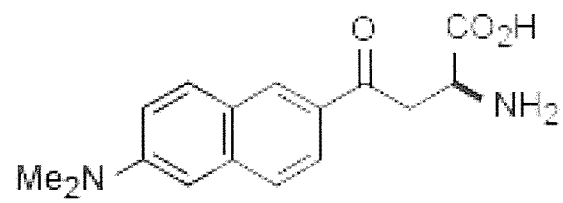
FIG. 1 shows structures of (a) Aladan, and (b) GB1 ([11]). Residues with Aladan substitutions are highlighted: Leu[7] and Ala[24]. Fc and Fab binding surfaces are also shown[9,10]. (c) SHG spectrum of Aladan adsorbed to a mica surface, in PBS.

The invention includes a system for making molecules, and proteins in particular, suitable for detection by a surface-selective nonlinear optical technique. A first use of the invention is for determining a protein's structure in real space and real time. A second use of the invention is to detect a protein or its activity (conformational change). A third use of the invention is for drug screening A further aspect of the present invention is measuring probe tilt angle orientation in an oriented protein.

We introduce a new class of probes—SH-active unnatural amino acids—and demonstrate their use for detecting biomolecules and structural changes by SHG. Aladan is demonstrated to be SH-active by studying it alone on a surface and incorporated into a protein, GB1, rendering the protein detectable. A structural change is observed when an Fc fragment is introduced to GB1, labeled with Aladan at Ala[24], and bound to IgG on a surface. No such change is observed if Aladan is substituted at Leu[7] instead. These results are consistent with a local conformational change of GB1, a change undetectable by fluorescence or X-ray crystallography. SHG with SH-active exogenous labels or unnatural amino acid probes is promising as a structural technique with high angular and temporal resolution. With a narrowly oriented protein population appropriately labeled, the technique could be used to determine conformational change in real time and space, site-by-site.

Second-harmonic generation (SHG) is highly sensitive to the net, average orientation of SH-active molecules on surfaces, and has recently emerged as a technique for detecting biomolecules and their conformational changes. As most biomolecules are not intrinsically SH-active, they must be labeled with probes to render them detectable. To date, exogenous probes have been used to do this, but second-harmonic-active unnatural amino acids offer important advantages for the long-range goal of precisely and directly determining structural changes in real time, and may be used for both buried and surface sites. Results of the first known SH-active unnatural amino acid, Aladan, are presented here. Aladan is found to be SH-active by detecting it at an interface, both alone and incorporated into the B1 domain of protein G (GB1), a globular immunoglobulin-binding protein, at both buried and exposed sites. The tilt angle of Aladan alone adsorbed on a mica surface is determined by polarization experiments, and its nonlinear polarizability $\alpha^{(2)}$ is found to be ca. $10^{-30}$ esu. Aladan GB1 mutants are detectable by SHG, either when coupled covalently to a derivatized glass surface or bound to IgG immobilized via protein A. Addition of an Fc domain to this GB1 complex causes a small but defined change in the SH signal when Aladan is incorporated at site Ala[24], but not at Leu[7], consistent with a local conformational change of GB1. This structural change is not apparent in either X-ray crystallography and fluorescence studies, demonstrating that SHG can detect subtle orientational changes, including protein-protein interactions in which no significant rearrangements occur.

Second-harmonic generation (SHG) is well known in the physical sciences for studying molecules on surfaces and is especially useful for measuring orientation. More recently, SHG has emerged as a sensitive technique to detect and study the conformational changes of biomolecules using SH-active probes[1,2]. Labeled proteins that are adsorbed or covalently immobilized on surfaces produce an SHG signal, which is due to the average, net orientation of the nonlinear polarizability of the SHG label relative to the surface plane. Specifically, the SH intensity is given as $I_{SH} = G(\chi_s^{(2)})^2 I^2$, where $I_{SH}$ is the second-harmonic intensity, G is a constant that depends on the experimental geometry and wavelength, and I is the intensity of the fundamental beam. The nonlinear susceptibility, $\chi_s^{(2)}$, carries the details of the SH-active molecules on the surface via the equation:

$$\chi_s^{(2)} = N_s \langle \alpha^{(2)} \rangle \quad (1)$$

where $N_s$ is the surface density of the molecules, the brackets denote an orientational average, and $\alpha^{(2)}$ is their nonlinear polarizability, a quantum-mechanical property that determines the probability of producing a second-harmonic photon from two, incident photons of the fundamental beam. Measurements of $\chi_s^{(2)}$ provide information about the orientation of a molecule on the surface. For example, when $\alpha^{(2)}$ is dominated by a single element $\zeta\zeta\zeta^{(2)}$ along the molecular axis $\zeta$ and the azimuthal distribution of the molecules are random in the plane of the surface, the only elements of $\chi_s^{(2)}$ that do not vanish are:

$$\chi_{s\perp\perp\perp}^{(2)} = N_s \langle \cos^3\theta \rangle \alpha_{\zeta\zeta\zeta}^{(2)} \quad (2A)$$

$$\chi_{s\perp\|\|}^{(2)} = \chi_{s\|\perp\|}^{(2)} = \chi_{s\|\|\perp}^{(2)} = \frac{1}{2} N_s \langle \cos\theta \sin^2\theta \rangle \alpha_{\zeta\zeta\zeta}^{(2)} \quad (2B)$$

where θ is the polar angle between ζ and the surface normal, and the subindices ⊥ and ∥ refer to the directions perpendicular and parallel to the surface, respectively[3].

The SH light is coherent and directional, so collection and isolation of the SH beam is simplified, and because the fundamental and the second-harmonic are well separated spectrally, cross-talk, which can plague fluorescence measurements, is non-existent with SHG. Photodegradation of the probe occurs relatively slowly via two-photon-induced absorption, allowing measurements over relatively long timescales. The trade-off with SHG is signal strength—it is orders of magnitude weaker than fluorescence. However, only SH-active molecules immobilized on the surface contribute second harmonic light since randomly diffusing molecules near the surface produce no signal; their orientational average, from Equation 1, is zero. Therefore, SHG is intrinsically equipped to discriminate between surface-bound and free molecules.

The SH signal reports on the orientational average of the probes, and thus changes due to conformational change. In previous work, ligand-induced conformational changes were detected by monitoring the SH intensity with calmodulin and adenylate kinase adsorbed non-specifically to surfaces[1,2]. SFG and SHG have also been applied to study protein adsorption phenomena at various interfaces with protein alone or co-adsorbed with an SH-active probe[4-8]. The current study uses GB1, a well-studied IgG-binding streptococcal protein that has been useful in a variety of structural and biophysical studies. GB1 binds to both the Fab and Fc domains of IgG, and structures of these complexes have been determined[9,10], in addition to that of the uncomplexed protein[11,12]. We have previously incorporated the synthetic amino acid Aladan at multiple sites of GB1 for studies of protein solvation[13,14] Like other donor-acceptor fluorophores, Aladan undergoes a large increase in dipole moment upon excitation, leading to significant solvatochromic fluorescence shifts.

Unnatural amino acids (UAA's) offer a means of labeling proteins at both buried and exposed sites, and as innate components of the protein they should report on structural changes with more sensitivity and fidelity than probes attached via sidechain-reactive linkers[13]. We report here that the synthetic amino acid Aladan shows good activity in SHG measurements, making it the first known SH-active UAA. We estimate the free Aladan hyperpolarizability to be $\sim 10^{-30}$ esu and measure the average orientation of Aladan adsorbed on a mica surface as 48°. Incorporated into GB1, we detect the protein when it is covalently coupled to a surface or bound via an IgG-protein A complex. Addition of Fc to the latter system causes a small change in the SH signal when Aladan is substituted at the Ala[24] residue, but not at Leu[7], consistent with a local change in GB1 conformation.

Measurements may be made using any suitable experimental set-ups and techniques. An exemplary set-up has been described previously[1,2]. Briefly, a Ti:S oscillator (Coherent; Mira 900) pumped by a solid-state DPSS laser (Spectra-Physics; 5W Millenia) was tuned to 780 nm (0.8 W) and focused into a prism (BK-7) that was optically coupled to the coverslips or mica surfaces for total internal reflection (TIR). The incident angle of the fundamental at the surface was 73° (critical angle=61°). A monochromator and color filter were used to remove the fundamental and select the SH signal and its intensity was measured by a PMT. A well for buffer was defined by an adhesive gasket (Grace Biolabs) and filled with phosphate buffered saline (PBS). Human IgG (normal serum) and Fc (IgG-Fc) were obtained from Bethyl Laboratories. Mica (Grade IV) was obtained from SPI Corporation and was freshly cleaved for the experiments. Protein A- and aldehyde-derivatized glass coverslips were obtained from Xenopore Corporation. Aladan and Aladan GB1 mutants (synthesized as described;[13,14] were introduced to the wells at 1 µM; IgG was added at 3 µM; and IgG-Fc was added at 6 µM. GB1-Aladan was immobilized on the aldehyde-derivatized surface by exposing the protein to the surface for several minutes followed by washing with buffer. For the experiments with IgG, the protein was incubated with the protein A coverslips for two hours followed by washing with PBS. All experiments except the measurements to determine $\chi^{(2)}$ were carried out with the fundamental p-polarized and the second-harmonic beam unpolarized.

We chose Aladan (FIG. 1A) for this SHG study because of its absorption wavelength, large Stokes shift and difference dipole moment[13]. The peak absorbance of Aladan in buffer is 390 nm[13] and the Δµ of its chromophore is large, variously estimated between 5 D[15] and 20 D[16]. Aladan was dissolved in methanol and exposed to a freshly cleaved mica surface and allowed to adsorb in PBS. An SH background of 3500 cps was measured, due to the mica surface and to water polarized in its vicinity ($\chi^{(2)}$ and $\chi^{(3)}$ contributions, respectively[17,18]). After several hours, the signal with Aladan reached a plateau of $\sim 10^6$ cps as shown in the SHG spectrum of 1C. The quadratic dependence of the SH signal on the fundamental power confirmed that Aladan is indeed SH-active. Two-photon-induced fluorescence, which appeared at ca. 550 nm, is well separated from the second harmonic light. Washing Aladan out of the well reverted the signal to the background level, demonstrating that the molecule adsorbs reversibly. The average orientation was determined by polarization measurements assuming a close packed monolayer of probe and a narrow orientational distribution. The SH intensity was measured as a function of input and output polarization to determine the nonlinear susceptibility elements $\chi_{zzz}^{(2)}$, $\chi_{zxx}^{(2)}$, and $\chi_{xzx}^{(2)}$ [3,19]. Ratios of the elements were used to calculate an average orientation of the probe on the mica surface of 48°. Power losses by the prism and the optics after the sample were taken into account in the calculation. The probe's nonlinear polarizability is estimated to be $\alpha^{(2)} \sim 10^{-30}$ esu.

Figure 1B:
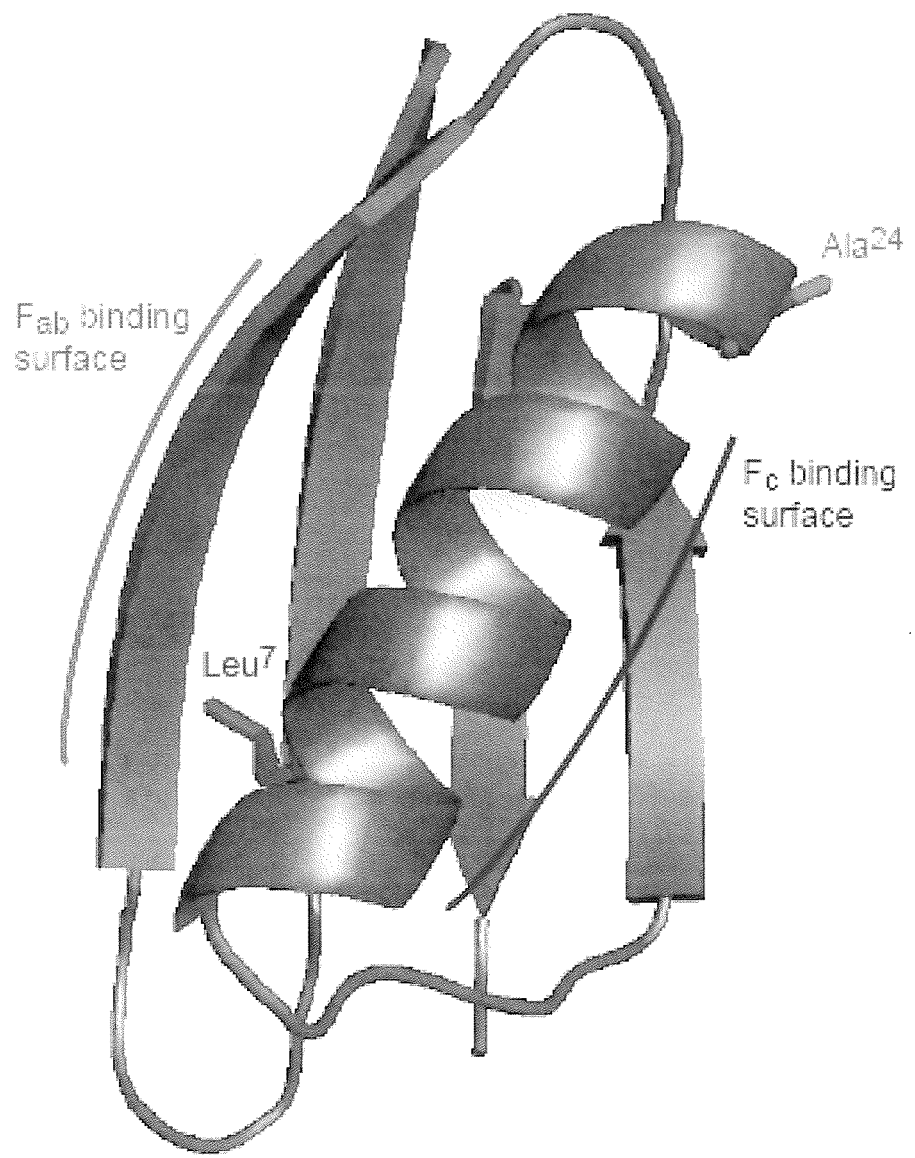
Figure 2A:
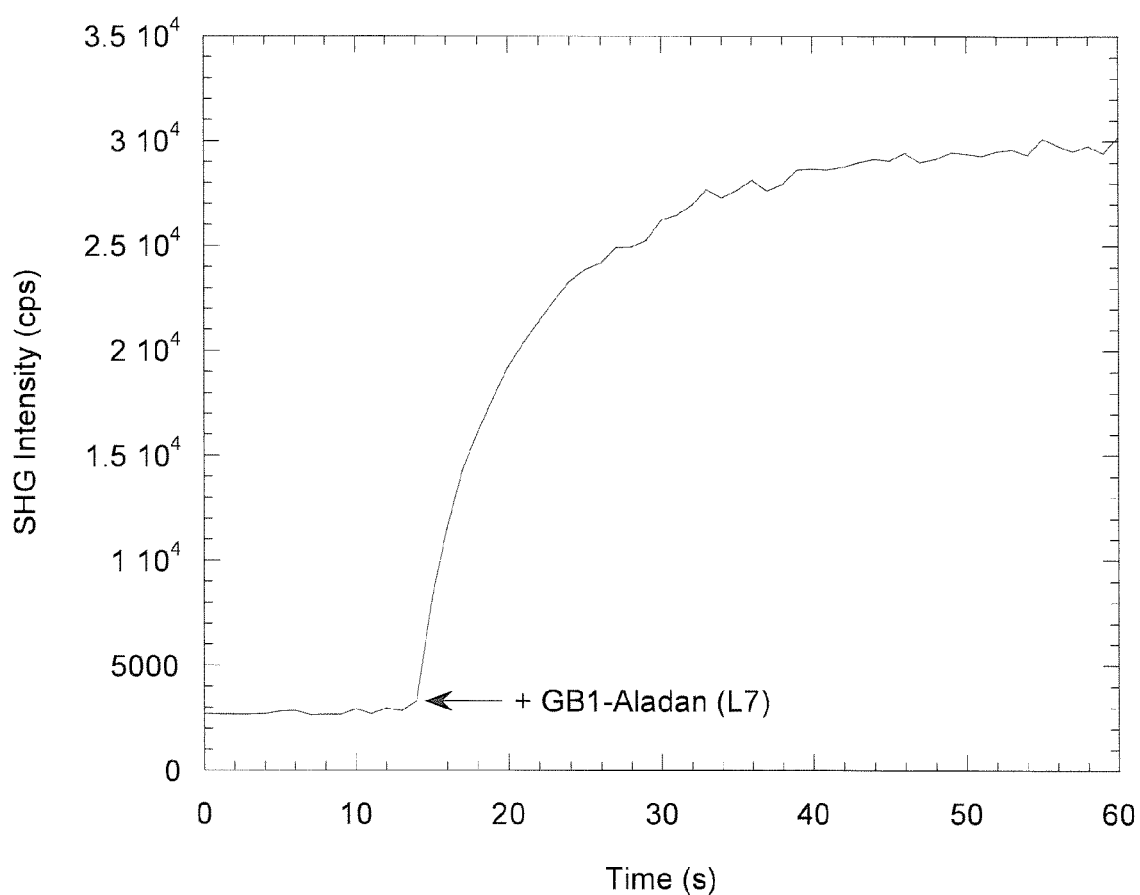
FIG. 2 shows SHG spectra for (a) GB1-Aladan adsorbing to an aldehyde-derivatized glass coverslip, detected by SHG, and plotted as SHG intensity versus time, and (b) the adsorbed protein at steady-state, detected by SHG, and plotted as SHG intensity versus wavelength.
Figure 2B:
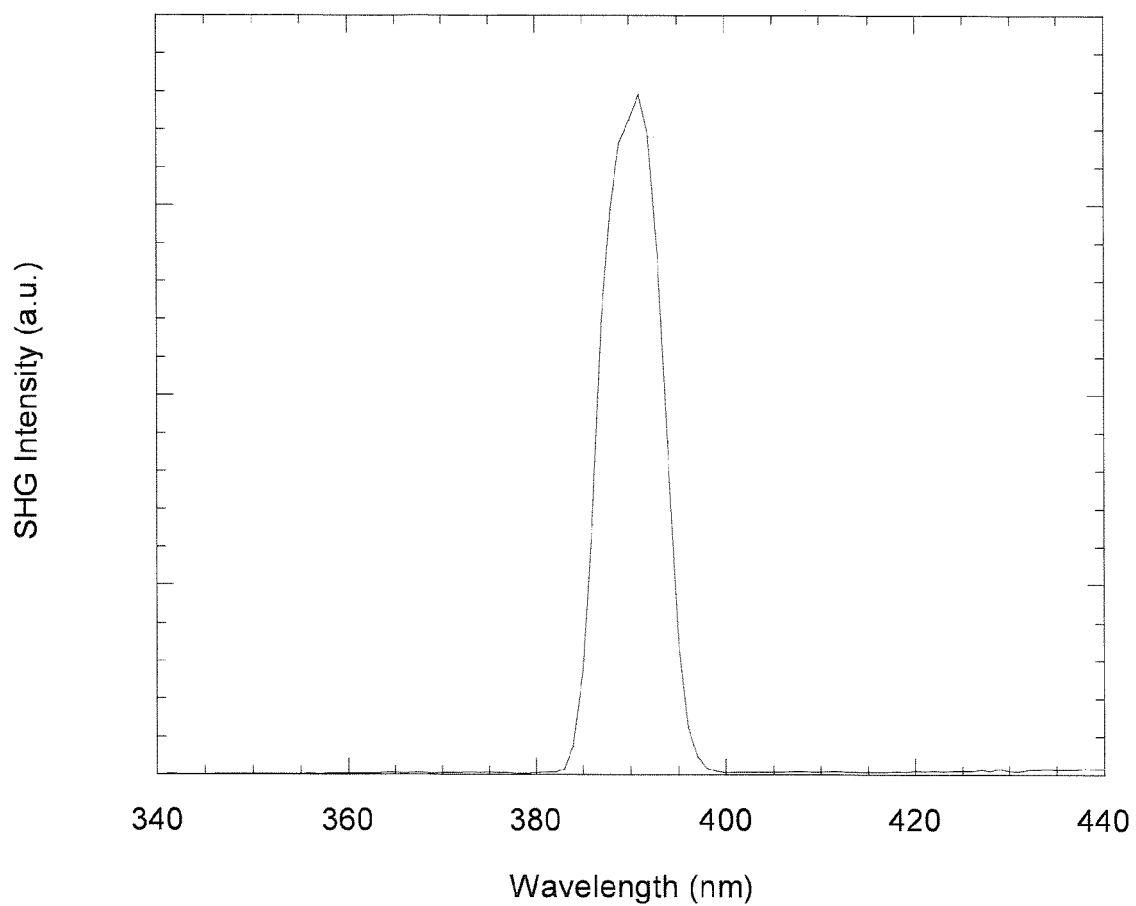

Next, Aladan mutants of the immunoglobulin-binding protein GB1 were used to show that an SH-active UAA can be used to detect protein on a surface. These Aladan-substituted proteins have previously been shown to fold and function similarly to wild-type GB1[13]. Aladan was incorporated at two positions as shown in FIG. 1B: Ala[24], a surface residue at the N-terminus of the helix and in proximity to the Fc binding surface, and Leu[7], a buried residue in the first β strand. An X-ray structure of the Fab-GB1 complex previously showed that Fab fragment binds edge-on to this first β strand[9]. The Ala[24] mutant was introduced into the well in contact with an aldehyde-derivatized coverslip. The SH signal immediately rose above the background as the GB1 lysines reacted with the aldehyde-derivatized surface (FIG. 2), reaching a plateau at about 30,000 cps. Wild-type GB1 produced no increase in the SH background upon addition (data not shown). The production of second-harmonic light by GB1-Aladan demonstrates that the protein self-orients to some degree upon binding to the surface, possibly due to the arrangement of lysines on the protein surface. The wavelength dependence of the signal shows the characteristic lineshape of the second-harmonic (FIG. 2B). The peak of Aladan absorption is ca. 390 nm, so the signal is resonantly enhanced. The SH signal after washing decreases slightly to 25,000 cps, indicating that some of the protein was reversibly bound to the surface.

Figure 3:
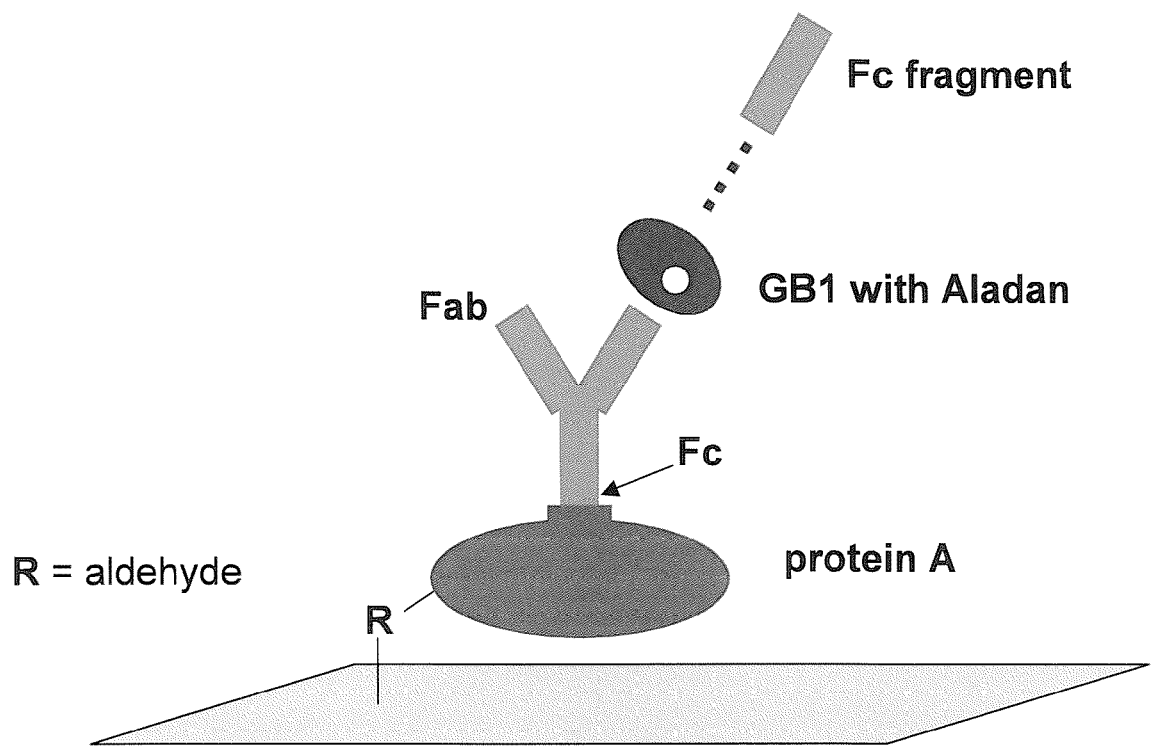
FIG. 3 shows a schematic view of the protein A-Fc-GB1 complex binding to the Fc fragment.
Figure 4A:
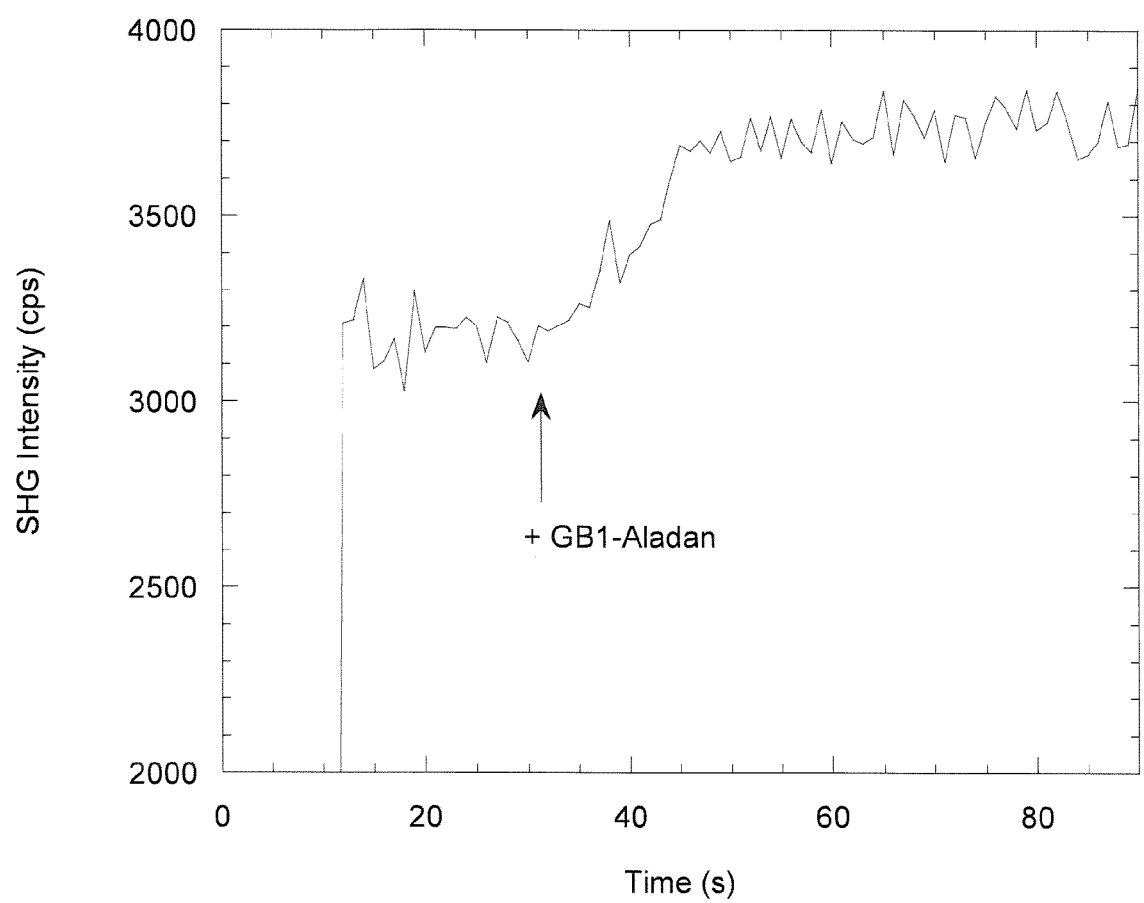
FIG. 4 shows SHG spectra for (a) GB1-Aladan binding to a IgG-Protein A-glass coverslip. (b) Addition of Fc causes a small decrease in SH signal with the Ala[24] Aladan mutant, indicating a change in the orientation of Aladan. (c) Addition of Fc to the Leu[7] Aladan mutant. Signals were detected by SHG and are averaged over 4 seconds. The bars denote the standard error of measurement (SEM).
Figure 4B:
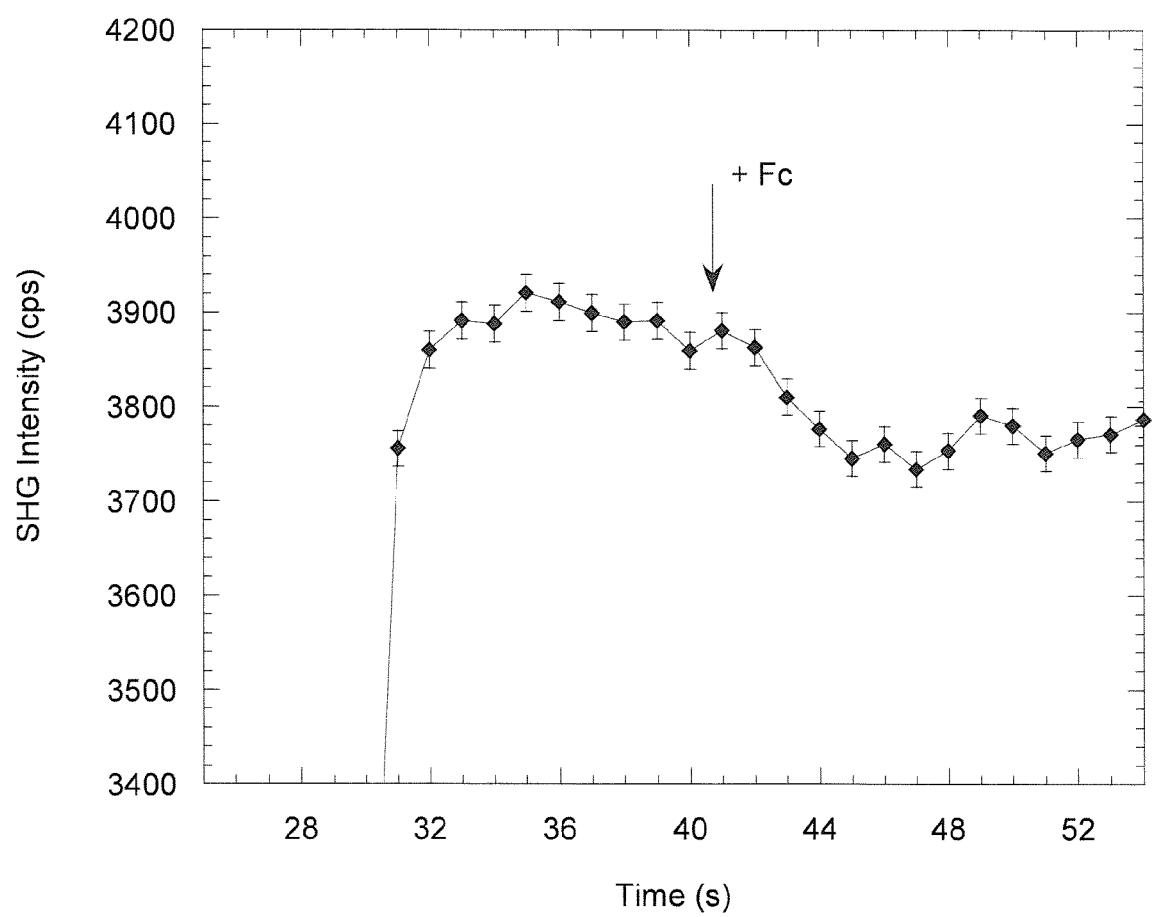
Figure 4C:
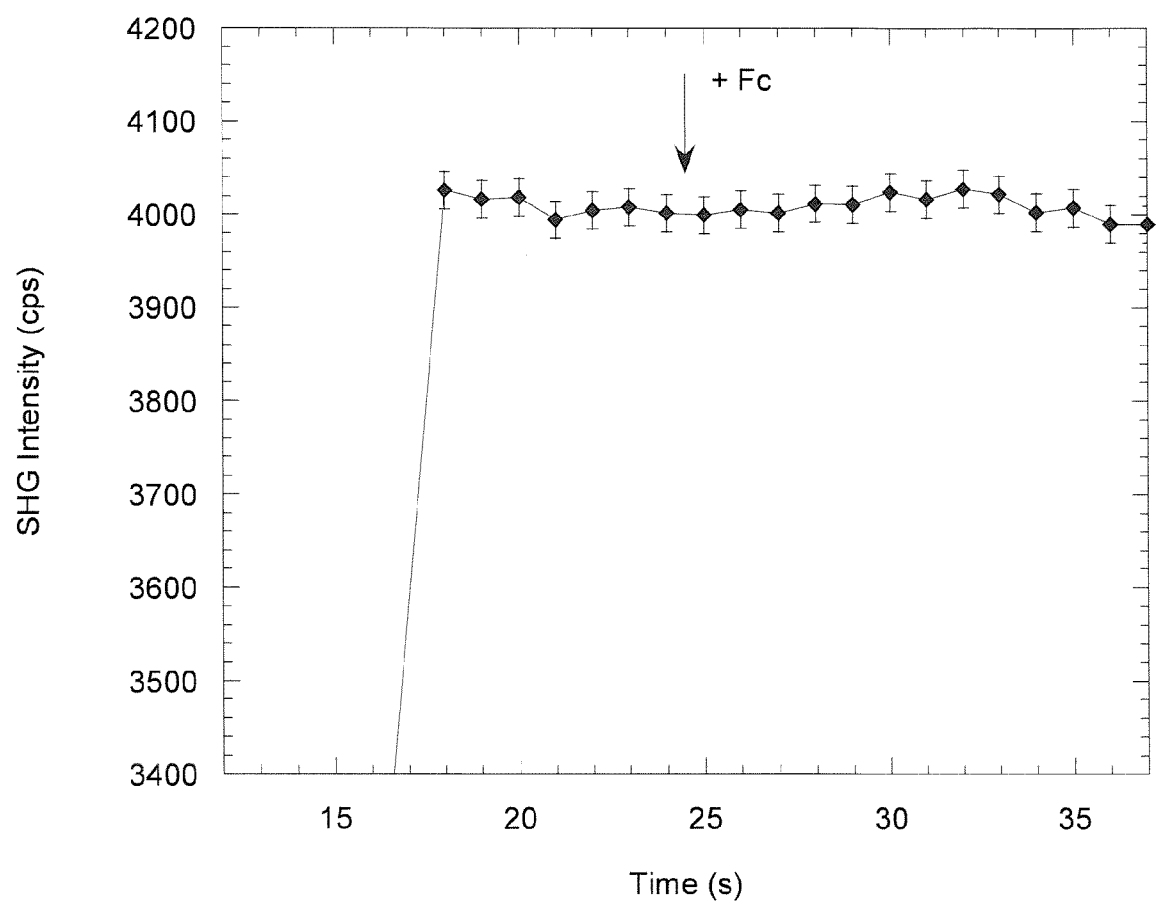

We next wanted to test whether SHG could detect any conformational change upon addition of Fc to GB1. X-ray structures of the Fc-GB1 and Fab-GB1 complexes show no global conformational changes compared to the uncomplexed GB1, though the modest resolution (3.5 Å) of the Fc-GB1 complex would make subtle changes difficult to detect. For this experiment, we used glass coverslips with protein A covalently coupled to their surface. These coverslips were incubated with IgG, which binds to protein A via its Fc domain as shown in FIG. 3. After washing, GB1 with Aladan substituted at Ala[24] was added for binding to the exposed IgG Fab domain, causing an increase in SH signal of ~600 cps as shown in FIG. 4A. In a control experiment, addition of Ala[24] mutant to protein A coverslips without IgG caused no increase in SH signal, indicating that GB1 binds specifically to IgG (data not shown). The much lower SH signal of GB1 bound to IgG-Protein A compared with to the aldehyde-derivatized surface is due to the reduced number of surface sites available for binding given the much larger size of the protein A-IgG complex than GB1 alone (>200 kDa for the complex vs. 6 kDa for GB1). Excess, unbound GB1 was then removed from the well by washing with PBS, but the SH signal remained constant. Addition of Fc causes a small and reproducible decrease in the SH signal (140±60 cps; 4 second average), which is detectable within the experimental noise, as shown in FIG. 4B. The SH signal of GB1-Aladan is remarkably stable over time on the protein-derivatized surfaces (no measurable change in signal over 10's of seconds) without the presence of an oxygen scavenger, indicating minimal photobleaching of the probe. As a control, Fc added to IgG-Protein A without GB1 produces no change in the SH background (data not shown). In another control, Aladan was incorporated at Leu[7], a buried site away from the Fc binding region. No change in SH signal was observed upon adding Fc to this mutant bound to IgG-Protein A (FIG. 4C).

SHG is directly sensitive to molecular orientation on surfaces and—by applying it to biological molecules—can measure subtle structural changes. The present work is motivated by the goal of using the technique to measure conformational change in real time and space as a function of probe location. An unnatural SH-active amino acid, a class of probes we introduce here, is used to detect GB1 and its conformational change upon binding Fc. There are few techniques available to study structural motion of biomolecules in real space. Fluorescence resonance energy transfer (FRET) is useful for detecting conformational changes[20-22], reporting on relative changes in distance and orientation between two site-specific probes, rather than absolute changes in structure. Other techniques, such as NMR and Raman spectroscopy, are useful for studying protein dynamics at a wide range of time scales[23-25]. These techniques rely on an interpretation of spectra to deduce structural changes and therefore do not provide direct real-space information, which may lead to uncertainty in model fitting. NMR has also traditionally been difficult to apply to larger biomolecules (e.g., >30 kDa) and membrane proteins, as well as on structural motions on slower, but functionally important, time scales (e.g., μs to ms). Environment-sensitive dyes have also been used to detect conformational changes, notably when a probe moves between polar and nonpolar environments, or whose distance from nearby quenchers changes[20,26-28]. SHG complements these techniques, for example, when it is difficult to incorporate multiple probes into a protein, or when the environment of a probe does not change appreciably with conformational change. SHG is relatively insensitive to quenching and to environmental changes, since it relies on a scattering process rather than emission. Most importantly, the technique is sensitive to absolute changes in probe orientation and has the potential to measure structural changes in real space and real time simultaneously. In the present study, we demonstrate that the free amino acid Aladan is SH-active by detecting it adsorbed to a mica surface. If the orientational distribution of Aladan is the same whether it is incorporated into GB1 or adsorbed directly to a surface, the expected difference in SH signal intensity between the two samples would be about two orders of magnitude apart since $I_{SH} \alpha N_s^2$; this is in rough agreement with the difference we measure. The signal strength in photons/pulse of surface SHG is governed by the following equation:

$$S \cong (256\pi^4 \omega / hc^3) |N_s \alpha^{(2)}|^2 I^2 AT \qquad (3)$$

I is the intensity of the fundamental beam incident at 45°, A is the beam cross section at the surface, T is the pulse duration, and ω is the second-harmonic frequency[29]. An regeneratively amplified system, of the type used to study ultrafast processes (e.g., μJ pulses)[30], increases the SHG signal by several orders of magnitude. With Aladan's $\alpha^{(2)}$ of ca. $10^{-30}$ esu, an amplified system, and standard noise reduction methods, the time resolution of the technique should be extendible to time scales of $10^{-6}$ s. To improve the time resolution, tighter focusing, higher fundamental peak power, or probes with higher nonlinear polarizability could be used. For example, a signal enhancement of about a factor of 5 could be achieved by tuning the incident angle of the fundamental to the critical angle[31]. Because the background is similar in magnitude to the GB1-Aladan signal and thus cannot be ignored, the relative phases of the various SH contributions must be known to quantitatively determine the absolute orientation of the probes or their angular change (Δ°) upon adding Fc.

Upon adding Fc to the surface-bound Ala$^{24}$ GB1 mutant, a small signal decrease occurs. Given the experimental noise levels in our set-up, the lower limit of this signal change is about 80 cps, indicating that a change in the average orientation of Aladan in GB1 occurs upon binding Fc. No observable change occurs in the same experiment with Aladan incorporated at Leu$^7$ (FIG. 4C), so these experiments are consistent with a local conformational change of GB1 at the N-terminus of the GB1 helix, rather than a reorientation of the IgG-GB1 complex. Alternatively, following Equation 2, the average orientation of the probe at Leu$^7$ may be much less sensitive to reorientation than when it is at Ala$^{24}$. In this case, the observed change in SH signal could indicate a reorientation of the Fab-GB1 complex when binding to Fc rather than a local conformational change. Structures of both wild-type GB1 and the GB1-Fc complex have been reported, with no apparent structural differences outside of minor sidechain movements in the binding pocket formed largely by the helix, and the 3$^{rd}$ β strand[10]. The Aladan substituted at Ala$^{24}$ would be expected to reside just outside of the binding pocket, which extends to Glu$^{27}$ on the helix. In contrast, there is no significant change in Ala$^{24}$ Aladan fluorescence upon Fc binding (B. Cohen, unpublished data). Compared to UAA's, exogenous probes, such as spin labels or fluorophores attached via sidechain-reactive linkers, are expected to reside farther from the binding pocket and have greater ranges of motion[28].

In this instance, SHG is able to detect a small signal change, a change not apparent in the protein by fluorescence or crystallography. With a highly oriented population of probes (and protein), the technique could resolve angular changes as small as 1°[1]. GB1, bound to Fab on the surface, is the first study by SHG of a protein specifically ordered on a surface (FIG. 3). The GB1-Fab interaction has been defined crystallographically and is likely to produce an ordered array of GB1 on the mica surface in the present study[9]. Combined with the absolute homogeneity of labeling arising from site-specific Aladan incorporation, this could provide a level of sensitivity necessary to sense to a conformational change not previously detected by other techniques. Detection of conformational changes have also been obtained with an integrin protein ($\alpha_\nu\beta_3$) and amyloid proteins (β-amyloid and α-synuclein) (J. Salafsky, unpublished data). Another major goal of this research is to quantitatively map conformational change of a biomolecule in real time. To achieve this requires a narrow, or at least a Gaussian distribution of the probes (and thus the protein)[32], and there are a variety of methods to specifically immobilize proteins to a surface (e.g., epitope tags, His-tags, antibody binding, etc.). Methods for orienting protein in 2-D in ways which preserve their functionality and freedom to move will be as indispensable to the technique as is growing crystals for X-ray studies. An important test for the technique is to measure the angular change that a site-specific probe undergoes upon ligand binding in a well defined system (e.g., maltose binding protein), and compare the result with that obtained by X-ray or NMR experiments.

The present invention discloses the use of unnatural amino acids which possess a hyperpolarizability for detecting proteins using a nonlinear technique such as second-harmonic generation. Henceforth, these specific unnatural amino acids will be referred to as SHAA's ('Second-Harmonic-Amino-Acid'). One advantage of using unnatural amino acids (AA's) as probes of protein is that detection can be carried out in vivo—that is, in live cells. For example, the invention could be used to detect conformational change or protein activation in live cells in response to binding of ligands or drugs. The invention could be used for drug screening for compounds that induce or block conformational change in a protein, in the cellular milieu, or which bind, for example, to specific conformations of the protein. By using an oriented protein population, relative to a surface, a highly precise map of structure or conformational change in real space and real time could be built, which would be of use to basic research concerning questions such as protein folding, structure, function and dynamics. The invention optionally may include screening a plurality of compounds (e.g., candidate ligands, drugs, and/or modulators) by sequentially and/or simultaneously assessing their effects on conformation and/or other measurable parameters, for example, using a sample holder such as a microplate having a plurality of sample sites supporting a corresponding plurality of samples or sample systems.

In the case of in vivo detection, the cell itself orients the protein of interest, as, for instance, with membrane receptors and ion channels. This net orientation is a crucial requirement for detection by the nonlinear optical schemes employed in the present invention—such as second-harmonic generation or sum-frequency generation.

There is a large and growing body of literature which describes a number of methods for incorporating unnatural amino acids—including fluorescent ones—into a variety of proteins in both prokaryotes and eukaryotes. For example, the papers of Schultz and coworkers[33,34], Dougherty and coworkers[35,36] and references therein describe the field. U.S. Pat. No. 7,045,337 also describes in detail how unnatural amino acids can be incorporated in vivo. Furthermore, there has been a report in the literature of an unnatural amino acid that is a good candidate for possessing a hyperpolarizability (Aladan) based on its large fluorescence Stokes shift[37]. The SHAA can be incorporated into proteins in E. coli, a prokaryote, a mammalian cells, S. cerevisiae, etc. Multiple SHAA's can be incorporated into a single protein by techniques known to those skilled in the art.

Whether a given unnatural amino acid possesses a hyperpolarizability can be tested in a number of ways known to those skilled in the art. For example, it can be predicted to occur computationally, tested by incubating the molecule for propensity to generate second-harmonic light when it is contacted with an interface, measured using hyperrayleigh scattering, measured by an EFISH experiment, and so on. However, the final test to determine whether an unnatural amino acid possesses a hyperpolarizability is the presence of second-harmonic emission from the probe within the protein itself.

One aspect of the present invention is the detection of a protein containing a SHAA by second-harmonic generation or sum-frequency generation: for example, detection in vitro at an interface, in vivo in cell membranes, or in vivo in the interior or the cells. With a well defined protein orientation, a protein's structure can be determined in real time and real space (e.g., conformational change detection) by measuring the tilt angle or absolute tilt angle of an unnatural amino acid probe, or a series of such probes, placed in different mutants of the protein. The probes can be incorporated at any site within the protein or at its termini, in any domain, etc. A third aspect of the invention includes a second-harmonic-active moiety or dye molecule that is chemically equipped to react covalently with an unnatural AA; for example, if the unnatural AA incorporated into a protein is Para-acetyl-phenylalanine (pAcF), the second-harmonic-active dye would have appropriate chemistry on it for bonding covalently to pAcF. A fourth aspect of the invention is the incorporation of a SHAA in addition to a second unnatural AA, the second unnatural AA (which will in general not be second-harmonic-active) allows chemically orthogonal covalent coupling of the protein in an oriented manner to a surface derivatized with appropriate chemistry for reaction with the second AA. With a highly oriented protein sample that is SH-active (using the two unnatural AA's), both the baseline SHG signal and the contrast (change in signal with conformational change) are larger.

Furthermore, a highly oriented protein population would enable the determination of the actual conformational change the SHAA undergoes upon conformational change, by determining the tilt angle of one or more probes at one or more sites within the protein as a function of time. The three-dimensional structure of a protein could be determined by making one or more mutants of a protein each containing a SHAA probe placed in a different location (i.e., the probe orientation relative to the surface in each mutant, and therefore the sidechain orientation, can be determined for the probe in each mutant and a model of the overall three dimensional protein structure could be built using this information). Information from steric hindrance methods, statistical methods, molecular dynamics, Ramachandran plots, or energy minimization methods known to those skilled in the art could be used to further aid in determining the structure given the measured probe tilt angles. A time-resolved measurement of the tilt angle of a probe produces a motion picture of a conformational change of a protein as it occurs in real time. Because of SHG's (and SFG's) virtually instantaneous response and sensitivity, spatial orientation of a particular probe (e.g., tilt angle or absolute tilt angle relative to a surface) could be measured in real time at almost any time scale of interest. Although the ideal probes could be unnatural amino acids, the present invention would also work with exogeneous dye probes that are well known in the state of the art (e.g., PyMPO-succinimidyl ester that couples to surface amines of a protein).

The use of an array of proteins on a surface would facilitate, for example, the rapid determination of conformational change in real time for basic research or drug screening, or the three-dimensional structure of a protein that is oriented on the surface, for example, by using a series of mutants arrayed on the surface, which each contain a SHAA probe in a different site of the protein. The absolute tilt angle of each probe can be determined using methods known to those skilled in the art. For example, the papers of Goh and Kemnitz and the papers that cite them describe how absolute tilt angles are measured[38,39]. The tilt angles of the probes in the different mutants, determined from their positions in the various sites in the mutant proteins, could thus be used to build a map of the protein's three-dimensional structure using techniques known to those skilled in the art, for example, by using computer modeling and energy minimization methods.

Second harmonic generation detection of a protein containing a SHAA is well known to those skilled in the art. The protein can be immobilized or adsorbed to a surface in such a way to produce a net orientation of the SHAA itself (its transition moment) and thus generate a source of second-harmonic radiation that can be detected in a straightforward manner. Conformational change of a protein containing a SHAA can be detected by adding ligands, drugs, etc. to the medium that is in contact with the surface (i.e., the interface) and monitoring a change in a physical property of the second-harmonic radiation (e.g., its intensity or polarization-dependence).

Important drug targets such as ion channels, integrins, kinases, receptors and GPCRs will all benefit from having a means of introducing a probe with a hyperpolarizability into them, without the need for chemical labeling in vitro. These mutant proteins could then be used for drug screening or basic research studies.

The SHAAs could, of course, also be used as probes of protein location or spatial dynamics within a cell. The present invention, of course, is not limited to proteins. Any biological molecule or entity into which an unnatural amino acid can be incorporated is covered by the scope of the invention.

For enzymes such as kinase or phosphatase protein[40-48], important conformational changes occur in loop regions, such as in the activation loop upon binding ligands or drugs. As these loop regions are typically mobile, as exhibited by the lack of order in these regions in the proteins' X-ray-determined structure, it is expected that they will well tolerate amino acid substitutions and/or labeling in or near these regions. The loop regions are well known to those skilled in the art of determining or using the structures of the proteins. Moreover, catalytic function of a kinase requires a conformational change of the 'activation loop'. As the active structures of kinase proteins across the kinome (there are about 500 distinct kinase proteins encoded by the human genome) are highly similar, drugs that target the active form of a kinase often are non-selective, reacting 'off-target' with other kinases. Loop regions that are well known in the art include catalytic loops, WPD loops, PTP loops, recognition loops and activation loops.

In this disclosure, a new class of probes is introduced—SH-active unnatural amino acids—and their use for detecting biomolecules and structural changes by SHG is demonstrated. Aladan is demonstrated to be SH-active by studying it alone on a surface and incorporated into a protein, GB1, rendering the protein detectable. A structural change is observed when an Fc fragment is introduced to GB1, labeled with Aladan at Ala[24] and bound to IgG on a surface. No such change is observed if Aladan is substituted at Leu[7] instead. These results are consistent with a local conformational change of GB1, a change undetectable by fluorescence or X-ray crystallography. SHG with SH-active exogenous labels or unnatural amino acid probes is promising as a structural technique with high angular and temporal resolution. With a narrowly oriented protein population appropriately labeled, the technique could be used to determine conformational change in real time and space, site-by-site.

EXAMPLES

The following examples further describe selected aspects and embodiments of the present disclosure. These examples and the various features and aspects thereof are included for illustration and are not intended to define or limit the entire scope of the present disclosure.

Example 1

An unnatural amino acid, Aladan, which possesses a hyperpolarizability, as determined by standard means known to those skilled in the art, is incorporated into maltose binding protein in *E. coli*, purified and expressed.

A baseline second-harmonic signal is generated using a Ti:Sapphire laser totally internally reflected from a suitable surface such as a polystyrene coverslip, available commercially from Newport Corp. or Coherent Inc. Details of the experimental set-up and recording of the data are described in Salafsky, 2006[3]. The surface is mounted on and index-matched to a prism through which the fundamental and second-harmonic beams pass. A rubber gasket is placed on the surface to define a well with a volume of about 100 microliters. Aqueous buffer is added to the well. The wavelength of the fundamental is tuned to about 720 nm and the power is maximized. The SH baseline is recorded continuously using a filter to block the fundamental beam, a photomultiplier and single-photon detection.

The maltose binding protein, with the incorporated second-harmonic-active probe, is then added to the buffer. The protein will adsorb to the surface and generate a second-harmonic beam at about 360 nm, which is then recorded as an increase in signal from the buffer-surface interface. Thus, second-harmonic detection of a protein that has an unnatural amino acid with a hyperpolarizability (a SHAA) is accomplished, in this case in vitro.

Example 2

An unnatural amino acid that is second-harmonic active is incorporated into a single site in 10 different adenylate kinase mutants, each with the probe in a different site, according to procedures known to those skilled in the art. The protein mutants are isolated and purified according to standard means. The mutants are optionally screened for both activity and ability to generate second-harmonic radiation at an interface to determine the kinase that is both most native-like (e.g., in Km, Vmax, etc.) and also competent for generating second-harmonic radiation. For generating the second-harmonic radiation, the kinase proteins are adsorbed to a polystyrene surface.

Example 3

A series of mutants of maltose binding protein, which each possess a SHAA probe at a unique site, is created. A his-tag at the C-terminus is used to orient the protein on a Ni-NTA-bearing lipid bilayer according to protocols known to those skilled in the art. The mutant proteins containing the probes are bound to the bilayer specifically via the His-tag to create a defined, oriented population of protein. The absolute tilt angle of the probe in each mutant is measured according to well-established procedures. The tilt angles of the probes measured by SHG are used to create a three-dimensional model of the side-chain orientation and, by modeling, the three-dimensional structure of the entire protein. This SHG determined structure can be then compared with the X-ray crystal structure to heuristically improve the modeling, if necessary. Addition of lactose will induce a conformational change in the protein that can be resolved as a motion picture in real space and real time by measuring the absolute tilt angle of the probe in one or more of the mutants.

The disclosure set forth above may encompass multiple distinct inventions with independent utility. The disclosure relates information regarding specific embodiments, which are included for illustrative purposes, and which are not to be considered in a limiting sense, because numerous variations are possible. The inventive subject matter of the disclosure includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

REFERENCES (1) Salafsky, J. S. *Journal of Chemical Physics* 2006, 125, 074701.
(2) Salafsky, J. S. *Physical Chemistry Chemical Physics* 2007, 9, 5704.
(3) Heinz, T. F.; Tom, H. W. K.; Shen, Y. R. *Physical Review A* 1983, 28, 1883.
(4) Salafsky, J. S.; Eisenthal, K. B. *Journal of Physical Chemistry B* 2000, 104, 7752.
(5) Polizzi, M. A.; Plocinik, R. M.; Simpson, G. J. *Journal of the American Chemical Society* 2004, 126, 5001.
(6) Paszti, Z.; Wang, J.; Clarke, M. L.; Chen, Z. *Journal of Physical Chemistry B* 2004, 108, 7779.
(7) Clarke, M. L.; Wang, J.; Chen, Z. *Journal of Physical Chemistry B* 2005, 109, 22027.
(8) Kriech, M. A.; Conboy, J. C. Using the intrinsic chirality of a molecule as a label-free probe to detect molecular adsorption to a surface by second harmonic generation Applied Spectroscopy, 2005; Vol. 59; pp 746.
(9) Derrick, J. P.; Wigley, D. B. *Nature* 1992, 359, 752.
(10) Sauereriksson, A. E.; Kleywegt, G. J.; Uhl, M.; Jones, T. A. *Structure* 1995, 3, 265.
(11) Gronenborn, A. M.; Filpula, D. R.; Essig, N. Z.; Achari, A.; Whitlow, M.; Wingfield, P. T.; Clore, G. M. *Science* 1991, 253, 657.
(12) Achari, A.; Hale, S. P.; Howard, A. J.; Clore, G. M.; Gronenborn, A. M.; Hardman, K. D.; Whitlow, M. *Biochemistry* 1992, 31, 10449.
(13) Cohen, B. E.; McAnaney, T. B.; Park, E. S.; Jan, Y. N.; Boxer, S. G.; Jan, L. Y. *Science* 2002, 296, 1700.
(14) Abbyad, P.; Shi, X. H.; Childs, W.; McAnaney, T. B.; Cohen, B. E.; Boxer, S. G. *Journal of Physical Chemistry B* 2007, 111, 8269.
(15) Samanta, A.; Fessenden, R. W. *Journal of Physical Chemistry A* 2000, 104, 8972.
(16) Weber, G.; Farris, F. J. *Biochemistry* 1979, 18, 3075.
(17) Berkovic, G.; Shen, Y. R.; Marowsky, G.; Steinhoff, R. *Journal of the Optical Society of America B-Optical Physics* 1989, 6, 205.
(18) Ong, S. W.; Zhao, X. L.; Eisenthal, K. B. *Chemical Physics Letters* 1992, 191, 327.
(19) Heinz, T. F. *Second-Order Nonlinear Optical Effects at Surfaces and Interfaces*; Elsevier: Amsterdam, 1991.
(20) Glauner, K. S.; Mannuzzu, L. M.; Gandhi, C. S.; Isacoff, E. Y. *Nature* 1999, 402, 813.
(21) Cha, A.; Snyder, G. E.; Selvin, P. R.; Bezanilla, F. *Nature* 1999, 402, 809.
(22) Majumdar, D. S.; Smirnova, I.; Kasho, V.; Nir, E.; Kong, X. X.; Weiss, S.; Kaback, H. R. *Proceedings of the National Academy of Sciences of the United States of America* 2007, 104, 12640.
(23) Thomas, G. J. J. Annual Review of Biophysics and Biomolecular Structure, 1999; Vol. 28; pp 1.
(24) Ishima, R.; Torchia, D. A. Protein dynamics from NMR Nature Structural Biology, 2000; Vol. 7; pp 740.
(25) Weljie, A. M.; Yamniuk, A. P.; Yoshino, H.; Izumi, Y.; Vogel, H. J. Protein conformational changes studied by diffusion NMR spectroscopy: Application to helix-loop-helix calcium binding proteins Protein Science, 2003; Vol. 12.

(26) Ghanouni, P.; Steenhuis, J. J.; Farrens, D. L.; Kobilka, B. K. *Proceedings of the National Academy of Sciences of the United States of America* 2001, 98, 5997.
(27) Weitzman, C.; Consler, T. G.; Kaback, H. R. *Protein Science* 1995, 4, 2310.
(28) Cohen, B. E.; Pralle, A.; Yao, X. J.; Swaminath, G.; Gandhi, C. S.; Jan, Y. N.; Kobilka, B. K.; Isacoff, E. Y.; Jan, L. Y. *Proceedings of the National Academy of Sciences of the United States of America* 2005, 102, 965.
(29) Chen, C. K.; Heinz, T. F.; Ricard, D.; Shen, Y. R. *Physical Review Letters* 1981, 46,1010.
(30) Zimdars, D.; Eisenthal, K. B. Static and Dynamic Solvation at the Air/Water Interface Journal of Physical Chemistry B, 2001; Vol. 105; pp 3993.
(31) Felderhof, B. U.; Bratz, A.; Marowsky, G.; Roders, O.; Sieverdes, F. *Journal of the Optical Society of America B-Optical Physics* 1993, 10, 1824.
(32) Feller, M. B.; Chen, W.; Shen, Y. R. *Physical Review A* 1991, 43, 6778.
(33) Xie, J. M. & Schultz, P. G. Innovation: A chemical toolkit for proteins—an expanded genetic code. Nature Reviews Molecular Cell Biology 7, 775-782 (2006).
(34) Summerer, D. et al. A genetically encoded fluorescent amino acid. Proceedings of the National Academy of Sciences of the United States of America 103, 9785-9789 (2006).
(35) Rodriguez, E. A., Lester, H. A. & Dougherty, D. A. In vivo incorporation of multiple unnatural amino acids through nonsense and frameshift suppression. Proceedings of the National Academy of Sciences of the United States of America 103, 8650-8655 (2006).
(36) England, P. M. Unnatural amino acid mutagenesis: A precise tool for probing protein structure and function. Biochemistry 43, 11623-11629 (2004).
(37) Cohen, B. E. et al. Probing protein electrostatics with a synthetic fluorescent amino acid. Science 296, 1700-1703 (2002).
(38) Goh, M. C. et al. Absolute Orientation of Water-Molecules at the Neat Water-Surface. Journal of Physical Chemistry 92, 5074-5075 (1988).
(39) Kemnitz, K. et al. The Phase of 2nd-Harmonic Light Generated at an Interface and Its Relation to Absolute Molecular-Orientation. Chemical Physics Letters 131, 285-290 (1986).
(40) Hubbard, S. R., Mohammadi, M. & Schlessinger, J. Autoregulatory mechanisms in protein-tyrosine kinases. Journal of Biological Chemistry 273, 11987-11990 (1998).
(41) Huse, M. & Kuriyan, J. The conformational plasticity of protein kinases. Cell 109, 275-282 (2002).
(42) Nagar, B. et al. Crystal structures of the kinase domain of c-Abl in complex with the small molecule inhibitors PD173955 and imatinib (STI-571). Cancer Research 62, 4236-4243 (2002).
(43) Noble, M. E. M., Endicott, J. A. & Johnson, L. N. Protein kinase inhibitors: Insights into drug design from structure. Science 303, 1800-1805 (2004).
(44) Seeliger, M. A. et al. High yield bacterial expression of active c-Abl and c-Src tyrosine kinases. Protein Science 14, 3135-3139 (2005).
(45) Sicheri, F. & Kuriyan, J. Structures of Src-family tyrosine kinases. Current Opinion in Structural Biology 7, 777-785 (1997).
(46) Sicheri, F., Moarefi, I. & Kuriyan, J. Crystal structure of the Src family tyrosine kinase Hck. Nature 385, 602-609 (1997).
(47) Xu, W. Q., Doshi, A., Lei, M., Eck, M. J. & Harrison, S. C. Crystal structures of c-Src reveal features of its autoinhibitory mechanism. Molecular Cell 3, 629-638 (1999).
(48) Xu, W. Q., Harrison, S. C. & Eck, M. J. Three-dimensional structure of the tyrosine kinase c-Src. Nature 385, 595-602 (1997).

The invention claimed is:

1. A method for determining if a local conformational change in the structure of a protein domain occurs upon exposing a protein to a second molecule, the method comprising:
(a) genetically incorporating a second harmonic (SH)-active or sum frequency (SF)-active unnatural amino acid into the protein domain to obtain a non-naturally occurring mutant of the protein;
(b) contacting the protein domain with an interface such that the SH-active or SF-active unnatural amino acid has a net orientation at the interface;
(c) detecting light emitted using a surface-selective technique; and
(d) measuring a change in one or more physical properties of the emitted light upon exposing the protein to the second molecule, wherein the change in one or more physical properties of the emitted light indicates a local conformational change in the structure of the protein domain.

2. The method of claim 1, wherein the protein is detected in vitro.

3. The method of claim 1, wherein the protein is detected in vivo.

4. The method of claim 1, wherein the second molecule is a ligand, a compound, a small molecule, a drug, a peptide, an inhibitor, or a protein.

5. The method of claim 1, further comprising comparing the value of the one or more physical properties measured, with the value of the one or more physical properties measured in the absence of exposure to the second molecule.

6. The method of claim 1, wherein the protein is immobilized on a surface.

7. The method of claim 6, wherein the surface is a glass surface or mica.

8. The method of claim 1, wherein the unnatural amino acid is Aladan.

9. The method of claim 1, wherein the protein is an ion channel, an integrin, a kinase, a phosphatase, a receptor, or a G-protein coupled receptor (GPCR).

10. The method of claim 9, wherein the protein is a kinase or a phosphatase.

11. The method of claim 10, wherein the domain of the protein that undergoes a conformational change upon binding to a second molecule is a loop region.

12. The method of claim 11, wherein the loop region is a catalytic loop, a WPD loop, a PTP loop, a recognition loop, or an activation loop.

13. The method of claim 1, wherein the one or more physical properties of the emitted light comprise intensity or polarization dependence.

14. A method for determining if a local conformational change in the structure of a protein domain occurs upon exposing a protein to a second molecule, the method comprising:
(a) genetically incorporating a first unnatural amino acid into the protein which is second harmonic (SH)-active or sum frequency (SF)-active to obtain a non-naturally occurring mutant of the protein;

(b) genetically incorporating a second unnatural amino acid into the protein-which is not SH-active or SF-active;
(c) chemically coupling the protein in an oriented manner to a surface by reacting the second unnatural amino acid with the surface;
(d) detecting light emitted using a surface-selective technique; and
(e) measuring a change in one or more physical properties of the emitted light upon exposing the protein to the second molecule, wherein the change in one or more physical properties of the emitted light indicates a local conformational change in the structure of the domain of the protein.

* * * * *